US010180430B2

(12) United States Patent
Franzmann et al.

(10) Patent No.: US 10,180,430 B2
(45) Date of Patent: Jan. 15, 2019

(54) METHODS FOR DETECTING HUMAN PAPILLOMAVIRUS AND PROVIDING PROGNOSIS FOR HEAD AND NECK SQUAMOUS CELL CARCINOMA

(71) Applicant: UNIVERSITY OF MIAMI, Miami, FL (US)

(72) Inventors: Elizabeth Franzmann, Miami, FL (US); Lutecia Pereira, Miami, FL (US); Isildinha M. Reis, Miami, FL (US); Robert C. Duncan, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 14/688,221

(22) Filed: Apr. 16, 2015

(65) Prior Publication Data
US 2015/0219656 A1    Aug. 6, 2015

Related U.S. Application Data

(62) Division of application No. 14/358,515, filed as application No. PCT/US2012/065282 on Nov. 15, 2012.

(60) Provisional application No. 61/559,974, filed on Nov. 15, 2011, provisional application No. 61/654,595, filed on Jun. 1, 2012.

(51) Int. Cl.
*G01N 33/574* (2006.01)

(52) U.S. Cl.
CPC ... *G01N 33/5743* (2013.01); *G01N 33/57488* (2013.01); *G01N 2333/025* (2013.01); *G01N 2333/70585* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 5,403,551 A | 4/1995 | Galloway et al. |
| 5,976,895 A | 11/1999 | Cipkowski |
| 6,235,470 B1 | 5/2001 | Sidransky |
| 6,379,620 B1 | 4/2002 | Tydings et al. |
| 6,548,019 B1 | 4/2003 | Lee et al. |
| 6,730,268 B2 | 5/2004 | Lee et al. |
| 8,088,591 B2 | 1/2012 | Franzmann et al. |
| 2002/0015964 A1 | 2/2002 | Streckfus et al. |
| 2004/0029114 A1 | 2/2004 | Mack et al. |
| 2005/0008646 A1 | 1/2005 | Young et al. |
| 2005/0214880 A1 | 9/2005 | Franzmann et al. |
| 2007/0185023 A1 | 8/2007 | Barnea |
| 2007/0190529 A1 | 8/2007 | Ridder et al. |
| 2009/0197285 A1 | 8/2009 | Hirschowitz et al. |
| 2009/0325201 A1 | 12/2009 | Franzmann et al. |
| 2012/0115165 A1 | 5/2012 | Franzmann et al. |
| 2014/0024042 A1 | 1/2014 | Franzmann et al. |
| 2014/0329230 A1 | 11/2014 | Franzmann et al. |

FOREIGN PATENT DOCUMENTS

| | | |
|---|---|---|
| CN | 1193280 | 9/1998 |
| CN | 1307681 | 8/2001 |
| CN | 1836166 | 9/2006 |
| CN | 101230390 | 7/2008 |
| WO | 2007/133725 | 11/2007 |
| WO | 2010/060103 | 5/2010 |
| WO | 2013/074793 | 5/2013 |

OTHER PUBLICATIONS

Franzmann et al. Soluble CD44 Is a Potential Marker for the Early Detection of Head and Neck Cancer. Cancer Epidemiol Biomarkers Prev 2007;16(7):1348-55.*
Hafkamp et al. A Subset of Head and Neck Squamous Cell Carcinomas Exhibits Integration of HPV 16/18 DNA and Overexpression of p16INK4A and p53 in the Absence of Mutations in p53 Exons 5-8. Int. J. Cancer: 107, 394-400 (2003).*
Liu et al. A timer-actuated immunoassay cassette for detecting molecular markers in oral fluids. Lab Chip, 2009, 9, 768-776.*
International Preliminary Report on Patentability from Application No. PCT/US2014/049223, dated Feb. 2, 2016, 6 pages.
Bourguignong, L.Y.W., et al., "CD44 Interaction with c-Src Kinase Promotes Cortactin-mediated Cytoskeleton Function and Hyaluronic Acid-dependent Ovarian Tumor Cell Migration," The Journal of Biological Chemistry, vol. 276, Issue 10, 2001, pp. 7327-7336.
Brocklehurst, P., et al., "Screening programmes for the early detection and prevention of oral cancer (Review)," The Cochrane Library, 2010, Issue 11, 2010, 30 pages.
Brown, L.R., et al., "The effect of radiation-induced xerostomia on saliva and serum lysozyme and immunoglobulin levels," Oral Surg Oral Med Oral Pathol, vol. 41, No. 1, 1976, pp. 83-92.
Delpech, B. et al., "Serum Hyaluronan (Hyaluronic Acid) in Breast Cancer Patients," International Journal of Cancer, vol. 46, 1990, pp. 388-390.
Forastiere, A., et al., "Head and Neck Cancer," New England Journal of Medicine, vol. 345, No. 26, 2001, pp. 1890-1900.
Fosang, A.J., et al., "An Elisa Plate Based Assay for Hyaluronan Using Biotinylated Proteoglycan G1 Domain (HA-Binding Region)," Matrix, vol. 10, Issue 5, 1990, pp. 306-313.
Franzmann, E.J., et al., "A novel CD44 v3 isoform is involved in head and neck squamous cell carcinoma progression," Otolaryngology Head and Neck Surgery, vol. 124, No. 4, 2001, pp. 426-432.
Franzmann, E.J., et al., "Expression of Tumor Markers Hyaluronic Acid and Hyaluronidase (HYAL1) in Head and Neck Tumors," International Journal of Cancer, vol. 106, 2003, pp. 438-445.
Franzmann, E.J., et al., Salivary Protein and solCD44 Levels as a Potential Screening Tool for Early Detection of Head and Neck Squamous Cell Carcinoma, Head & Neck, vol. 34, Issue 5, 2011, pp. 687-695.
Franzmann, E.J., et al. "Soluble CD44 is a potential marker for the early detection of head and neck cancer", Cancer Epidemiol Biomarkers Prev. Jul. 2007; 16(7):1348-55.
Franzmann, E.J., et al., Salivary Soluble CD44: A Potential Molecular Marker for Head and Neck Cancer, Cancer Epidemiology Biomarkers & Prevention, vol. 14, 2005, pp. 735-739.

(Continued)

*Primary Examiner* — Nianxiang Zou
(74) *Attorney, Agent, or Firm* — Meunier Carlin & Curfman LLC

(57) ABSTRACT

Methods and kits for diagnosing and determining prognosis of head and neck squamous cell carcinoma are described.

17 Claims, 12 Drawing Sheets

(56) References Cited

OTHER PUBLICATIONS

Harris, E.K., "Effects of Intra- and Interindividual Variation on the Appropriate Use of Normal Ranges," Clinical Chemistry, vol. 20, Issue 12, 1974, pp. 1535-1542.
Hu, S., et al., "Salivary Proteomics for Oral Cancer Biomarker Discovery," Clinical Cancer Research, vol. 14, No. 19, 2008, pp. 6246-6252.
Li, Y., et al., "Salivary Transcriptome Diagnostics for Oral Cancer Detection," Clinical Cancer Research, vol. 10, 2004, pp. 8442-8450.
Lingen, M.W., et al., "Critical Evaluation of Diagnostic Aids for the Detection of Oral Cancer," Oral Oncology, vol. 44, Issue 1, 2008, pp. 10-22.
Lingen, M.W., et al., "Squamous cell carcinoma of the head and neck in nonsmokers: clinical and biologic characteristics and implications for management," Current Opinion in Oncology, vol. 13, 2001, pp. 176-182.
Lokeshwar, V.B., et al., "Urinary Hyaluronic Acid and Hyaluronidase: Markers for Bladder Cancer Detection and Evaluatoin of Grade," The Journal of Urology, vol. 163, 2000, pp. 348-356.
Mahfouz, M.E., et al., "Current potential and limitations of molecular diagnostic methods in head and neck cancer," Eur Arch Otorhinolaryngology, vol. 267, 2010, pp. 851-860.
Nagler, R.M., "Saliva as a tool for oral cancer diagnosis and prognosis," Oral Oncology, vol. 45, Issue 12, 2009, pp. 1006-1010.
O'Hara, J., et al., Head and neck cancer: a screening strategy, Clinical Otolaryngology and Allied Sciences, vol. 27, Issue 3, 2002, pp. 133-134.
Park, N.J., et al., "Salivary microRNA: Discovery, Characterization and Clinical Utility for Oral Cancer Detection," Clinical Cancer Research, vol. 15, No. 17, 2009, pp. 5473-5477.
Patton, L.L., et al., "Adjunctive Techniques for Oral Cancer Examination and Lesion Diagnostics: A Systematic Review of the Literature," Journal of the American Dental Association, vol. 139, 2008, pp. 896-905.
Patton, L.L., "The effectiveness of community-based visual screening and utility of adjunctive diagnostic aids in the early detection of oral cancer," Oral Oncology, vol. 39, Issue 7, 2003, pp. 708-723.
Pereira, L.H., et al., "Salivary markers and risk factor data: A multivariate modeling approach for head and neck squamous cell carcinoma detection," Cancer Biomarkers, vol. 10, No. 5, 2012, pp. 241-249.
Pham, H.T., Tumor-derived Hyaluronidase: A Diagnostic Urine Marker for High-Grade Bladder Cancer, Cancer Research, vol. 57, 1997, pp. 778-783.
Reed, A.H., et al., "Influence of Statistical Method Used on the Resulting Estimate of Normal Range," Clinical Chemistry, vol. 17, No. 4, 1971, pp. 275-284.
Sankaranarayanan, R., et al., "Early Findings from a Community-Based, Cluster-Randomized, Controlled Oral Cancer Screening Trial in Kerala, India," Cancer, vol. 88, No. 3, 2000, pp. 664-673.
Sankaranarayanan, R., et al., Effect of screening on oral cancer mortality in Kerala, India: a cluster-randomised controlled trial, Lancet, vol. 365, 2005, pp. 1927-1933.
Sartor, M.A., et al., "Genome-wide methylation and expression differences in HPV(+) and HPV (−) squamous cell carcinoma cell lines are consistent with divergent mechanisms of carcinogenesis," Epigenetics, vol. 6, No. 6, 2011, pp. 777-787.
Smart, C.R., "Screening for Cancer of the Aerodigestive Tract," Cancer, vol. 72, No. 3, 1993, pp. 1061-1065.
Stern, M., et al., "An ELISA-Like Assay for Hyaluronidase and Hyaluronidase Inhibitors," Matrix, vol. 12, 1992, pp. 397-403.
Sugiyama, M., et al., "Non-invasive detection of bladder cancer by identification of abnormal CD44 proteins in exfoliated cancer cells in urine," Journal of Clinical Pathology: Molecular Pathololgy, vol. 48, 1995, pp. M142-M147.
Tockman, M. S., et al., "Considerations in Bringing a Cancer Biomarker to Clinical Application," Cancer Research, vol. 52, 1992, pp. 2711s-2718s.

Vokes, E.E., et al., "Head and Neck Cancer," The New England Journal of Medicine, vol. 328, No. 3, 1993, pp. 184-194.
First Examination Report, dated Nov. 19, 2014, received in connection with Australian Application No. 2013203539.
First Examination Report, dated Oct. 29, 2013, received in connection with corresponding Australian Application No. 2013200514.
International Search Report and Written Opinion, dated Nov. 12, 2014, received in connection with International Application No. PCT/US2014/049223.
International Search Report and Written Opinion, dated Feb. 7, 2013, received in connection with International Application No. PCT/US2012/065282.
International Search Report and Written Opinion, dated Oct. 24, 2007, received in connection with International Application No. PCT/US2007/011511.
U.S. Appl. No. 12/300,523, filed Feb. 20, 2009 (now U.S. Pat. No. 8,088,591, issued Jan. 3, 2012).
Non-final Office Action, dated Jan. 19, 2011, received in connection with U.S. Appl. No. 12/300,523, filed Feb. 20, 2009 (now U.S. Pat. No. 8,088,591, issued Jan. 3, 2012).
Non-final Office Action, dated Oct. 29, 2010, received in connection with U.S. Appl. No. 12/300,523, filed Feb. 20, 2009 (now U.S. Pat. No. 8,088,591, issued Jan. 3, 2012).
U.S. Appl. No. 13/324,526, filed Dec. 13, 2011.
Non-final Office Action, dated Sep. 10, 2014, received in connection with U.S. Appl. No. 13/324,526, filed Dec. 13, 2011.
U.S. Appl. No. 14/034,916, filed Sep. 24, 2013.
Final Office Action, dated Sep. 2, 2014, received in connection with U.S. Appl. No. 14/034,916, filed Sep. 24, 2013.
Non-final Office Action, dated Apr. 7, 2014, received in connection with U.S. Appl. No. 14/034,916, filed Sep. 24, 2013.
Non-final Office Action, dated Nov. 19, 2013, received in connection with U.S. Appl. No. 14/034,916, filed Sep. 24, 2013.
Final Office Action dated Mar. 5, 2015 from related U.S. Appl. No. 13/324,526, filed Dec. 13, 2011.
Non-Final Office Action dated Jun. 29, 2015 from corresponding U.S. Appl. No. 14/358,515, filed May 15, 2014.
Translation of First Office Action dated Apr. 28, 2015, from corresponding Chinese Application No. 201280067010.6, 3 pages.
Extended European Search Report dated Jun. 15, 2015, from corresponding European Application No. 12850526.0, 18 pages.
Non-Final Office Action dated May 21, 2015 from related U.S. Appl. No. 14/034,916, filed Sep. 24, 2013, 15 pages.
Non-Final Office Action dated Jun. 11, 2015 from related U.S. Appl. No. 14/034,916, filed Sep. 24, 2013, 9 pages.
Hafkamp et al. "A Subset of Head and Neck Squamous Cell Carcinomas Exhibits Intergration of HPV 16/18 DNA and Overexpression of p16INK4A and p53 in the Absence of Mutations in p53 Exons 5-8", Int. J. Cancer: 107, pp. 394-400 (2003).
Liu et al. "A timer-actuated immunoassay cassette for detecting molecular markers in oral fluids", Lab Chip, 2009, 9, pp. 768-776.
Speel, E-J M., et al. "Molecular evidence for a clonal relationship between multiple lesions in patents with unknown primary adenocarcinoma," International Journal of Cancer, vol. 123, 2008, pp. 1292-1300.
Office Action, dated Sep. 1, 2015, received in connection with CO U.S. Appl. No. 14/127,975. (English Translation).
European Search Report, dated Jun. 15, 2015, received in connection with EP Patent Application No. 12850526.0.
Non-final Office Action, dated Jun. 11, 2015, received in connection with U.S. Appl. No. 14/034,916.
Non-final Office Action, dated May 21, 2015, received in connection with U.S. Appl. No. 14/034,916.
Search Report, dated Jun. 2, 2015, received in connection with CN Patent Application No. 201280067010. (English Translation).
Office Action, dated Apr. 28, 2015, received in connection with CN Patent Application No. 201280067010. (English Translation).
English Translation of Third Office Action received in connection with Chinese Application No. 201280067010.6, dated Jul. 4, 2016, 9 pages.
English Translation of Office Action received in connection with Japanese Application No. 2014542462, dated Sep. 13, 2016, 2 pages.

(56) References Cited

OTHER PUBLICATIONS

Office Communication received in connection with European Application No. 12850526.0, dated Oct. 28, 2016, 5 pages.
English Translation of Office Action dated Nov. 30, 2016, for IL Application No. 232,556, 5 pages.
English Translation of Office Action dated Dec. 21, 2016, from CN Application No. 201480050455.2, 4 pages.
Duffort, Lola, "University of Miami Scientists Are Developing a 'Rinse and Spit' Test for Oral Cancers," Miami Herald, May 23, 2014 (XP055359578) Retrieved from the Internet: on Jul. 5, 2017.
Office Action dated Jul. 26, 2017, issued in Chinese Application No. 2014800504552.
European Search Report dated Aug. 1, 2017, issued in Application No. 14832653.1.
Office Action dated Nov. 16, 2017, issued in U.S. Appl. No. 15/196,514.
Office Action received in co-pending U.S. Appl. No. 14/908,822, dated Mar. 12, 2018.
Office Action issued in co-pending U.S. Appl. No. 15/227,382, dated Mar. 2, 2018.
Office Action received in Japanese Application No. 2016-531905, dated Apr. 24, 2018. English Translation included.
Communication Pursuant to Article 94(3) EPC, received in European Application No. 14832653.1, dated May 24, 2018.
Mayer, et al., "Increased soluble CD44 concentrations are associated with larger tumor size and lymph node metastasis in breast cancer patients", J Cancer Res Clinic Oncol (2008) 134: 1229-1235.
Office Action issued in corresponding U.S. Appl. No. 15/227,382, dated Mar. 2, 2018.
Office Action dated Nov. 9, 2018, from related Canadian Application No. 2,855,971, 6 pages.
Betz, et al. "Re-expression of hSNF5/INI1/BAF47 in pediatric tumor cells leads to G1 arrest associated with induction f p16ink4a and activation of RB", Oncogene, vol. 21, pp. 5193-5203, 2002.

\* cited by examiner

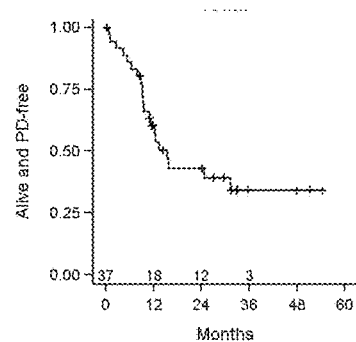
*FIGURE 1A*
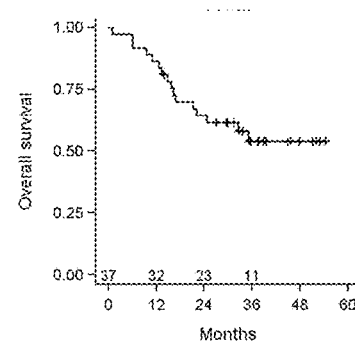
*FIGURE 1B*
|  | PFS | OS |
|---|---|---|
| Median | 15.4 months (9.6, --) | Not attained |
| 12-mon rate | 60.3% (42.3, 74.3%) | 86.5% (70.5, 94.1%) |
| 24-mon rate | 43.1% (25.8, 59.2%) | 64.3% (46.6, 77.5%) |
| 36-mon rate | 34.3% (17.7, 51.5%) | 53.8% (35.4, 69.0%) |
*FIGURE 1C*
|  |  | N | Median | Min | Max | Mean | Std |
|---|---|---|---|---|---|---|---|
| os_mon | All | 37 | 29.8 | 1.0 | 54.4 | 28.6 | 14.7 |
|  | Dead | 16 | 15.2 | 1.0 | 35.0 | 16.2 | 9.2 |
|  | Alive | 21 | 37.4 | 13.9 | 54.4 | 38.1 | 10.2 |
| pfs_mon | All | 37 | 11.7 | 0.3 | 54.4 | 17.5 | 14.2 |
|  | pd | 16 | 28.3 | 0.3 | 54.4 | 26.5 | 16.1 |
|  | No pd | 21 | 9.4 | 0.8 | 31.2 | 10.6 | 7.2 |
*FIGURE 1D*

METHODS FOR DETECTING HUMAN PAPILLOMAVIRUS AND PROVIDING PROGNOSIS FOR HEAD AND NECK SQUAMOUS CELL CARCINOMA

CROSS-REFERENCE TO RELATED APPLICATIONS

This application is a Divisional application of U.S. application Ser. No. 14/358,515 filed on May 15, 2014, which is a 371 of International Application No. PCT/US2012/065282 filed on Nov. 15, 2012, which claims the benefit of U.S. Provisional Application No. 61/559,974, filed Nov. 15, 2011, and to U.S. Provisional Application No. 61/654,595, filed Jun. 1, 2012, each of which is incorporated herein by reference in its entirety.

ACKNOWLEDGMENT OF GOVERNMENT SUPPORT

This invention was made with government support from the National Institutes of Health under grant No. R01CA118584-NIH. The government has certain rights in this invention.

FIELD

The subject matter disclosed herein generally relates to methods and kits for the detection, treatment, and prognosis of head and neck squamous cell carcinoma.

BACKGROUND

Head and neck squamous cell carcinoma (HNSCC) affects 50,000 people in the United States and 600,000 people world-wide each year. The main risk factors include tobacco and alcohol use and human papillomavirus (HPV) infection.

To date, there is no widely accepted HNSCC screening program or test (see, e.g., Vokes et al., *N Engl J Med,* 328:184-94 (1993); Lingen et al., *Curr Opin Oncol,* 13:176-82 (2001); Forastiere et al., *N Engl J Med* 345:1890-1900 (2001); Patton, *Orol Oncol,* 39:708-723 (2003); O'Hara et al., *Clin Otolaryngol,* 27:133-4 (2002); Smart, *Cancer* 72:1061-5 (1993); Sankaranarayanan et al., *Cancer,* 88:664-73 (2000); Sankaranarayanan et al., *Lancet* 365:1927-33 (2005)) because the gold standard, screening by physical exam followed by biopsy, has limited sensitivity and specificity (64% and 74%, respectively) (Brocklehurst et al., *Cochrane Database Syst Rev,* 11:CD004150 (2010)) and molecular diagnostic tests are still under development (Nagler, *Oral Oncol.,* 45:1006-10 (2009); Mahfouz et al., *Eur Arch Otorhinolaryngol,* 267:851-60 (2010)). Adjunctive techniques for oral cancer detection that use dyes, autofluorescence, or exfoliative cytology are available, but recent reviews question whether they improve early detection rates (Patton et al., *J Am Dent Assoc,* 139:896-905 (2008); Lingen et al., *Oral Oncol* 44:10-22 (2008)). Therefore, efforts have focused on molecular diagnostic tools. Several studies that tested saliva for RNA expression profiles (Li et al., *Clin Cancer Res,* 10:8442-8450 (2004)), microRNA discovery (Park et al., *Clin Cancer Res,* 15:5473-5477 (2009)) and proteomic analysis (Hu et al., *Clin Cancer Res,* 14:6246-6252 (2008)) show promise but are somewhat complicated and not validated (Nagler, *Oral Oncol.,* 45:1006-10 (2009); Mahfouz et al., *Eur Arch Otorhinolaryngol,* 267:851-60 (2010)). As a result, the majority of patients are diagnosed at a late stage, when cure rates are 40% or lower. Thus, early detection tests are needed.

SUMMARY

In accordance with the purposes of the disclosed materials, compounds, compositions, and methods, as embodied and broadly described herein, the disclosed subject matter, in one aspect, relates to methods and kits for detecting, treating, and providing a prognosis for head and neck squamous cell carcinoma.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

FIGS. 1A to 1B are graphs showing progression free survival (PFS) (FIG. 1A) and overall survival (OS) (FIG. 1B) of patients in study. FIG. 1C is a table showing median PFS, and rate of PFS and OS at 12, 24, and 36 months. FIG. 1D is a table showing OS and PFS total, medial, minimum, maximum, mean, and standard deviation.

Figure 6:
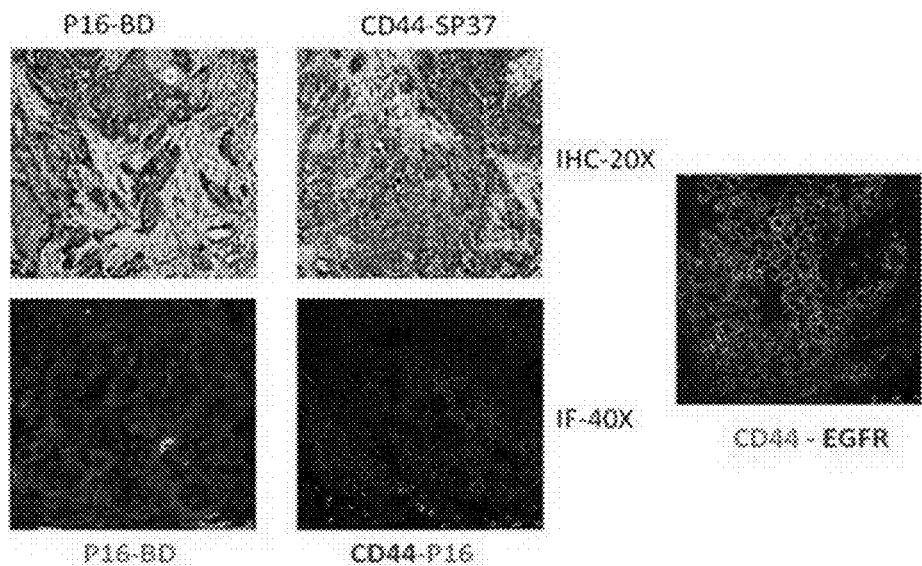

FIG. 6 shows immunohistochemistry (IHC) staining of p16, CD44, and EGFR in p16− cancer where p16 staining is cytoplasmic and diffuse. In this case, CD44 stains in the membrane and universally throughout the tumor. CD44 and EGFR colocalize on the cell membrane and there is some cytoplasmic staining of EGFR as well.

Figure 7:
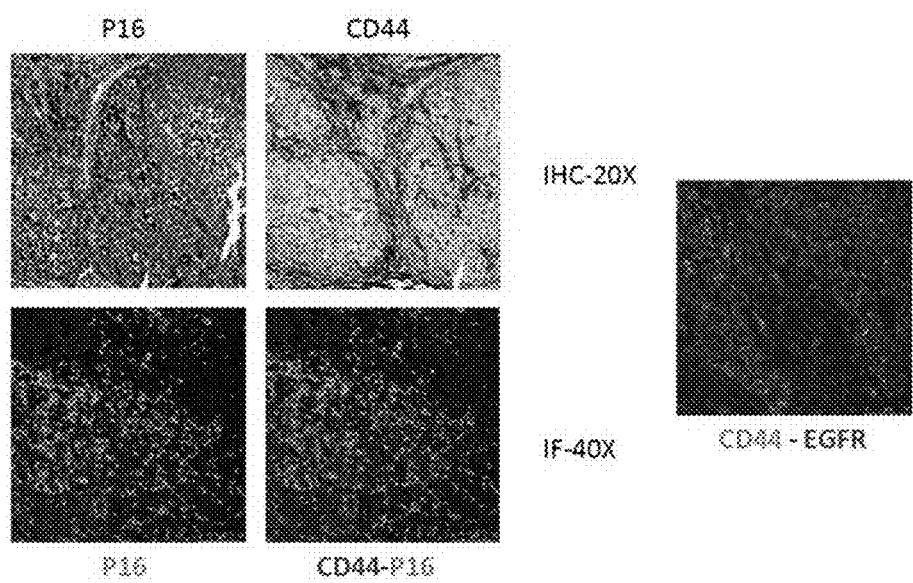

FIG. 7 shows IHC staining of p16, CD44, and EGFR in p16+ tumors where nuclei stain strongly for p16 and there is some cytoplasmic staining as well. However, CD44 membrane staining is lost, only the invading lymphocytes retain CD44 expression. EGFR expression is not seen at all.

DETAILED DESCRIPTION

The materials, compounds, compositions, and methods described herein may be understood more readily by reference to the following detailed description of specific aspects of the disclosed subject matter, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. "About" can mean within 5% of the stated value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "2000" is disclosed, then "about 2000" is also disclosed. It is also understood that when a value is disclosed, then "less than or equal to" the value, "greater than or equal to the value" and possible ranges between values are also disclosed, as appropriately understood by the skilled artisan. For example, if the value "2000" is disclosed, then "less than or equal to 2000" as well as "greater than or equal to 2000" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound comprising 2 parts by weight of component X and 5 parts by weight component Y, X and Y are present at a weight ratio of 2:5, and are present in such ratio regardless of whether additional components are comprised in the composition.

A weight percent (wt. %) of a component, unless specifically stated to the contrary, is based on the total weight of the formulation or composition in which the component is included.

The term "individual," "host," "subject," and "patient" are used interchangeably to refer to any individual who is the target of diagnosis, prognosis, administration, or treatment. The subject can be a vertebrate, for example, a mammal Thus, the subject can be a human or veterinary patient.

A "biomarker" is any gene or protein whose level of expression in a tissue or cell is altered compared to that of a normal or healthy cell or tissue.

The term "prognosis" is recognized in the art and encompasses predictions about the likely course of disease or disease progression, particularly with respect to likelihood of disease remission, disease relapse, tumor recurrence, metastasis, and death. "Good prognosis" refers to the likelihood that a patient afflicted with cancer, such as head and neck squamous cell carcinoma, will remain disease-free (i.e., cancer-free). "Poor prognosis" is intended to mean the likelihood of a relapse or recurrence of the underlying cancer or tumor, metastasis, or death. Cancer patients classified as having a "good outcome" remain free of the underlying cancer or tumor. In contrast, "bad outcome" cancer patients experience disease relapse, tumor recurrence, metastasis, or death. In particular embodiments, the time frame for assessing prognosis and outcome is, for example, less than one year, one, two, three, four, five, six, seven, eight, nine, ten, fifteen, twenty or more years. As used herein, the relevant time for assessing prognosis or disease-free survival time begins with the surgical removal of the tumor or suppression, mitigation, or inhibition of tumor growth. Thus, for example, in particular embodiments, a "good prognosis" refers to the likelihood that a head and neck squamous cell carcinoma patient will remain free of the underlying cancer or tumor for a period of at least five, more particularly, a period of at least ten years. In further aspects of the invention, a "bad prognosis" refers to the likelihood that a head and neck squamous cell carcinoma patient will experience disease relapse, tumor recurrence, metastasis, or death within less than five years, more particularly less than ten years. Time frames for assessing prognosis and outcome provided above are illustrative and are not intended to be limiting.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

Also, disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. This concept applies to all aspects of this disclosure including, but not limited to, compositions and steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Reference will now be made in detail to specific aspects of the disclosed materials, compounds, compositions, components, devices, articles, and methods, examples of which are illustrated in the following description and examples, and in the figures and their previous and following description.

Biomarker Assays

Efficient, inexpensive, noninvasive assays for diagnosing and determining prognosis for head and neck squamous cell carcinoma (HNSCC) are described. The disclosed assays involve the detection of one or more biomarkers, such as CD44 (e.g., soluble CD44 (solCD44), in a sample from the subject. U.S. Pat. No. 8,088,591 by Franzmann et al. is incorporated by reference in its entirety for its description of biomarkers that can be used to diagnose and monitor HNSCC in a subject. Elevated levels of these biomarkers are able to distinguish cancer patients from controls with high accuracy and specificity. However, these biomarkers are reduced in certain subject populations despite the presence of HNSCC.

Thus, disclosed are additional biomarkers and risk factors that may be used to improve the accuracy and specificity of an HNSCC assay. For example, it has been shown that solCD44 and total protein levels combined are more effective at distinguishing HNSCC from controls than either marker alone. However, solCD44 levels can be lower in subjects with human papillomavirus (HPV) infection. In fact, bivariate analysis using solCD44 and total protein levels works best in black men, wherein HPV infection is less common Therefore, inclusion of HPV status in a multivariate analysis can improve sensitivity and accuracy of the assay and allow for detection of HPV$^+$ HNSCC.

Other biomarkers associated with HNSCC detection or prognosis may be used in combination with total protein, solCD44, and HPV detection to improve sensitivity and/or accuracy of the disclosed method. For example, solCD44 levels can vary based on age and smoking status. Examples of HNSCC risk factors and demographic factors that may be used in the multivariate analysis include tobacco exposure, alcohol exposure, race, ethnicity, dental health, gender, level of education, age, general health, family history of cancer, sexual history and socioeconomic status and using the one or more risk factors or demographic factors in the multivariate analysis to determine the combined score.

Therefore, assays, and methods of using the assays for diagnosis and prognosis, are disclosed that involve multivariate analysis of the disclosed biomarkers and risk factors to determine a combined score for an individual subject. The combined score can then be used to determine the presence of HNSCC, or the risk of reoccurrence of HNSCC in a subject. In particular, cut-off combined score values can be determined empirically by comparing positive and negative control values.

The biomarkers described herein include genes and proteins. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides. Fragments and variants of biomarker genes and proteins are also encompassed by the present invention. By "fragment" is intended a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs.

The biomarkers described herein are genes and proteins whose overexpression correlates with cancer, particularly HNSCC, prognosis. In particular embodiments, selective overexpression of a biomarker or combination of biomarkers of interest in a patient sample is indicative of a poor cancer prognosis. By "indicative of a poor prognosis" is intended that overexpression of the particular biomarker or combination of biomarkers is associated with an increased likelihood of relapse or recurrence of the underlying cancer or tumor, metastasis, or death, as defined herein above. For example, "indicative of a poor prognosis" may refer to an increased likelihood of relapse or recurrence of the underlying cancer or tumor, metastasis, or death within five years, more particularly ten years. Biomarkers that are indicative of a poor prognosis may be referred to herein as "bad outcome biomarkers." In other embodiments, the absence of overexpression of a biomarker or combination of biomarkers of interest is indicative of a good prognosis. As used herein, "indicative of a good prognosis" refers to an increased likelihood that the patient will remain cancer-free, as defined herein above. In some embodiments, "indicative of a good prognosis" refers to an increased likelihood that the patient will remain cancer-free for at least five, more particularly at least ten years. Such biomarkers may be referred to as "good outcome biomarkers."

The disclosed biomarkers include genes and/or proteins whose overexpression (compared to a control) correlates with HNSCC prognosis. A gene or protein can be overexpressed by 10%, 20%, 30%, 40%, 50%, 60%, 70%, 80%, 90%, 100%, 200%, 300%, 400%, 500%, or greater as compared to a control. Biomarkers include genes and proteins that are indicative of a poor HNSCC prognosis (i.e., bad outcome biomarkers) as well as those that are indicative of a good prognosis (i.e., good outcome biomarkers). Biomarkers of particular interest include genes and proteins that are involved in regulation of cell growth and proliferation, cell cycle control, DNA replication and transcription, apoptosis, signal transduction, angiogenesis/lymphogenesis, or metastasis. In some embodiments, the biomarkers regulate protease systems involved in tissue remodeling, extracellular matrix degradation, and adjacent tissue invasion. Other biomarkers include regulators of gene expression such as hypermethylation or microRNA. Although any biomarker whose expression pattern is indicative of HNSCC prognosis can be used to practice the disclosed methods and assays, in particular embodiments, biomarkers are selected from the group consisting of HPV, total protein, and CD44. In one embodiment, the CD44 biomarker is solCD44.

HPV infection can be determined by measuring HPV directly or indirectly. Three categories of molecular assays are currently available for detection of HPV infection in tissue and exfoliated cell samples. All are based on detection of HPV DNA and include: (1) non-amplified hybridization assays (Southern transfer hybridization, (STH), dot blot hybridization (DB) and in situ hybridization (ISH)); (2) Signal amplified hybridization assays such as hybrid capture assays; and (3) Target amplification assays, such as PCR and in situ PCR. Southern blot hybridization requires large amounts of DNA, is laborious, and is not reproducible, while in situ hybridization has only moderate sensitivity for HPV. PCR-based detection of HPV is both extremely sensitive and specific. Using this approach, the viral DNA is amplified in vitro by DNA polymerase to generate adequate amount of target, which is then either directly visualized on gels, or (the more specific approach) detected by specific probe using traditional hybridization methods. In practice, the sensitivity of PCR based method is about 10-100 HPV viral genomes in a background of 100 ng cellular DNA. Since PCR can be performed on very small amounts of DNA (10-100 ng), it is ideal for use on specimens with low DNA content.

Currently, the only available FDA approved HPV detection method is the Hybrid capture II assay (Qiagen, Valencia, Calif.). In this assay HPV DNAs are hybridized to RNA probes, and RNA-DNA hybrids are captured and detected by a chemiluminescent system. The sensitivity of this assay is similar to that of PCR based assays, with high sensitivity being achieved by signal, rather than target amplification. The current HC II assay has the sensitivity to detect 1 pg HPV (about 50,000 copies) per ml sample. Proper sample collection is essential to achieve maximal sensitivity, and a brush-sampling device has been shown to be optimal. The HC II assay contains synthetic RNA probes complementary to the genomic sequence of 13 high-risk (types 16, 18, 31, 33, 35, 39, 45, 51, 52, 56, 58, 59, and 68) and 5 low-risk (6, 11, 42, 43, 44) HPV types.

Alternatively, HPV infection may be determined be detecting viral mRNA transcripts or through detection of the cellular protein p16. For HPV to cause cancer, persistent infection and a cellular environment that allows for high level expression of viral oncogenes E6 and E7 (initially in the basal cell layer and then throughout the epithelium) is necessary. Therefore, detection of E6/E7 mRNA may identify more clinically significant infection than a DNA approach.

Cyclin-dependent kinase inhibitor 2A, (CDKN2A, $p16^{Ink4A}$, p16) is a cellular correlate of the increased expression of oncogenic E6/E7 mRNA. The main actions of the HPV oncogenes are the degradation of p53 by E6 and thereby the abrogation of apoptosis as well as the release of E2F from pRb that leads to continuous activation of the cell cycle. Physiologically, E2F activation is mediated by phosphorylation of the Rb protein. This pathway is strictly regulated by a set of cyclin dependent kinase inhibitors, among them p16, that block enzymes phosphorylating pRB (cyclin dependent kinases). In cells with transforming HPV infections, the regulation of the Rb-E2F pathway is disturbed by E7 and the activation of p16 has no downstream effect. As a result, p16 is strongly overexpressed and accumulates in the cells. p16 overexpression has been demonstrated in the vast majority of cervical precancers and cancers while in normal tissue, p16 expression is found only rarely.

Epigenetic effects of HPV infection may also be used to detect HPV. Differentially methylated loci between HPV$^+$ and HPV$^-$ HNSCC cell lines are described in Sartor M A, et al. *Epigenetics* 6(6):777-87 (2011), which is incorporated by reference for these epigenetic profiles.

Therefore, HPV infection can be detected using antibodies that specifically bind $p16^{INK4a}$. Alternatively, HPV infection can be determined by detecting HPV DNA, RNA, or protein. Likewise, HPV infection can be determined by detecting viral oncogenes (e.g., E6/E7) or epigenetic changes.

Methods

Disclosed are methods for diagnosing HNSCC in a subject, staging an HNSCC tumor in a subject, monitoring efficacy of an HNSCC treatment, or determining the prognosis of a subject diagnosed with HNSCC, or predicting recurrence of HNSCC in a subject. These methods each comprise assaying a body sample from the subject for the presence of total protein, solCD44, and HPV. The combination of total protein, HPV, and CD44 levels may be used in a multivariate analysis to determine a combined score. The method may further comprise assaying the body sample for the presence of hyaluronic acid (HA), hyaluronidase (HAase), IL-8, or a combination thereof. HNSCC risk factors and/or demographic factors may also be used in combination with total protein, solCD44, and HPV detection to improve sensitivity and/or accuracy of the disclosed method.

Multivariate analysis is based on the statistical principle of multivariate statistics, which involves observation and analysis of more than one statistical outcome variable at a time. For example, there are several regression methods that can be used with multivariate analysis, including, but not limited to generalized linear and nonlinear regressions, logistic and Poisson regressions, supervised machine learning algorithms, neural networks, support vector machines, response surface modeling, and multivariate adaptive regression splines. In some embodiments, logisitic regression is used.

For example, the multivariate analysis can first involve determining how total protein, solCD44, and p16 levels change based on risk variables such as race, gender, smoking and alcohol use. Mathematical models may then be developed whose terms include biomarker levels and the risk variables to predict the probability of cancer. The statistical significance associated with the terms reflect their importance for prediction. A mathematical model may then be used to estimate a predictive score, which allows one to develop an overall probability score of cancer. For example, after having investigated how the marker levels and risk variables (e.g., race, gender, smoking and alcohol use) are associated with the outcome, including interactions, a fitted model can be obtained relating the log-odds of biomarkers and covariates. Based on this model, a score or a predictive probability for having cancer can be estimate at specified values of all variable included in the model.

In some embodiments, an increase in combined (predictive) score above a cut-off point distinguishes subjects with HNSCC from those without HNSCC or at low risk of future occurrence thereof. In some embodiments, an increase in combined score above a cut-off point identifies HNSCC tumor stage, predicts effectiveness of an HNSCC treatment, predicts prognosis of a subject diagnosed with HNSCC, or predicts the risk of HNSCC recurrence. For example, an increase in score above a cut-off point may be associated with a poor prognosis or likelihood of recurrence.

The disclosed assays and methods may be used to guide therapeutic treatment of a subject with HNSCC or at risk of developing HNSCC. For example, a subject with a low combined score may be given a single modality treatment such as surgery or radiation alone rather than combined therapy. This would result in decreased treatment-related morbidity. In contrast, a subject with a high combined score may be offered more aggressive treatments, such as surgery, radiation and chemotherapy, since higher treatment-related morbidity would be warranted given the higher risk of death from the disease. Therefore, the disclosed methods may further comprise treating a subject diagnosed with HNSCC or determined to have a poor HNSCC prognosis, with surgery, radiation therapy, chemotherapy, photodynamic therapy, targeted therapy, or any combination thereof Each of the disclosed biomarkers can be detected in a subject using body samples. By "body sample" is intended any sampling of cells, tissues, or bodily fluids in which expression of a biomarker can be detected. Examples of such body samples include but are not limited to blood, lymph, urine, gynecological fluids, biopsies, and smears. Bodily fluids useful in the present invention include blood, urine, saliva, nipple aspirates, lavages or any other bodily secretion or derivative thereof. Blood can include whole blood, plasma, serum, or any derivative of blood. In preferred embodiments, the body sample comprises oral rinses. Methods for collecting various body samples are well known in the art.

The methods are useful in detecting individuals at risk for head and neck cancer, including, for example, smokers, alcohol abusers, and subjects exposed to HPV virus. The methods described herein also permit the enhanced assessment of HNSCC prognosis in comparison to analysis of other known prognostic indicators. In particular aspects, the sensitivity and specificity is equal to or greater than that of known cancer prognostic evaluation methods. The endpoint for assessing specificity and sensitivity is comparison of the prognosis or outcome predicted using the methods of the invention (i.e., at or near the time of diagnosis) with the actual clinical outcome (i.e., whether the patient remained cancer-free or suffered a recurrence within a specified time period). As used herein, "specificity" refers to the level at which a method of the invention can accurately identify true negatives. In a clinical study, specificity is calculated by dividing the number of true negatives by the sum of true negatives and false positives. By "sensitivity" is intended the level at which a method of the invention can accurately identify samples that are true positives. Sensitivity is calculated in a clinical study by dividing the number of true positives by the sum of true positives and false negatives. In some embodiments, the sensitivity of the disclosed methods for the evaluation of HNSCC is at least about 40%, 45%, 50%, 55%, 60%, 65%, 70%, 75%, 80%, 85%, 90%, 91%, 92%, 93%, 94%, 95%, 96%, 97%, 98%, 99% or more. Furthermore, the specificity of the present methods is preferably at least about 40%, 45%, 50%, 55%, 60%, 65%, 70%, 75%, 80%, 85%, 90%, 91%, 92%, 93%, 94%, 95%, 96%, 97%, 98%, 99% or more. In further embodiments, the combined sensitivity and specificity value for the prognostic methods of the invention is assessed. By "combined sensitivity and specificity value" is intended the sum of the individual specificity and sensitivity values, as defined herein above. The combined sensitivity and specificity value of the present methods is preferably at least about 105%, 110%, 115%, 120%, 130%, 140%, 150%, 160% or more.

As used herein, the definitions of "true" and "false" positives and negatives will be dependent upon whether the biomarker or combination of biomarkers under consideration are good outcome or bad outcome biomarkers. That is, in the case of good outcome biomarkers (i.e., those indicative of a good prognosis), "true positive" refers to those samples exhibiting overexpression of the biomarker of interest, as determined by a physical exam followed by biopsy. A positive biopsy on pathology can indicate whether a sample is positive or negative.

As described above, in some embodiments, two or more biomarkers are used, more preferably, two or more complementary biomarkers. By "complementary" is intended that detection of the combination of biomarkers in a body sample results in the accurate determination of cancer prognosis in a greater percentage of cases than would be identified if only one of the biomarkers was used. Thus, in some cases, a more accurate determination of cancer prognosis can be made by using at least two of the disclosed biomarkers.

Any methods available in the art for detecting expression of biomarkers are encompassed herein. The expression of a biomarker of the invention can be detected on a nucleic acid level or a protein level. By "detecting expression" is intended determining the quantity or presence of a biomarker gene or protein. Thus, "detecting expression" encompasses instances where a biomarker is determined not to be expressed, not to be detectably expressed, expressed at a low level, expressed at a normal level, or overexpressed. In order to determine overexpression, the body sample to be examined can be compared with a corresponding sample. For example, a corresponding body sample that originates from a healthy person. That is, the "normal" level of expression is the level of expression of the biomarker in, for example, a sample from a human subject or patient not afflicted with HNSCC. The body sample can also be compared with a corresponding body sample from a subject treated for HNSCC. Such a sample can be present in standardized form. In some embodiments, determination of biomarker overexpression requires no comparison between the body sample and a corresponding body sample that originates from a healthy person. For example, detection of overexpression of a biomarker indicative of a poor prognosis in a tumor sample may preclude the need for comparison to a corresponding sample that originates from a healthy person. Moreover, in some aspects of the invention, no expression, underexpression, or normal expression (i.e., the absence of overexpression) of a biomarker or combination of biomarkers of interest provides useful information regarding the prognosis of a patient.

Methods for detecting expression of the biomarkers of the invention comprise any methods that determine the quantity or the presence of the biomarkers either at the nucleic acid or protein level. Such methods are well known in the art and include, but are not limited to, lateral flow "test strips," western blots, northern blots, southern blots, ELISA, immunoprecipitation, immunofluorescence, flow cytometry, immunohistochemistry, nucleic acid hybridization techniques, nucleic acid reverse transcription methods, and nucleic acid amplification methods, for example, PCR. In particular embodiments, expression of a biomarker is detected on a protein level using, for example, antibodies that are directed against specific biomarker proteins. These antibodies can be used in various methods such as Western blot, ELISA, immunoprecipitation, or immunohistochemistry techniques. Likewise, immunostaining of tissue can be combined with assessment of clinical information, conventional prognostic methods, and expression of molecular markers (e.g., $p16^{INK4a}$ and solCD44) known in the art. In this manner, the disclosed methods can permit the more accurate determination of HNSCC prognosis.

Kits

Also provided herein are kits for diagnosing a subject with HNSCC or determining the prognosis of a subject with HNSCC. The kit can include means for measuring $p16^{INK4a}$, solCD44, and/or total protein. For example, the kit can include a plurality of antibodies that specifically bind $p16^{INK4a}$. In some embodiments, the antibody comprises the idiotype of the E6H4 antibody clone. The kit can further include a detection agent (e.g., secondary antibodies and/or colorimetric agent) for detecting the contained antibodies. The kit can further include a plurality of antibodies that specifically bind CD44 (e.g., solCD44). The kit can further include a reagent for determining total protein concentration in a sample. The kit can also include a reference sample of $p16^{INK4a}$ and/or solCD44. The kit can additionally include directions for use of the kit (e.g., instructions for diagnosing a subject), a container, and/or a carrier. In particular, the kit can contain a computer readable medium or a hyperlink that uses algorithms and reference tables to convert detection values into a combined score. In some embodiments, the kit is a lateral flow immunoassay. Alternatively, the kit can comprise a multi-well plate, optionally coated with the antibody that specifically binds $p16^{INK4a}$ the antibody that specifically binds CD44, or a combination thereof.

The examples below are intended to further illustrate certain aspects of the methods and compositions described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1

The relationship between the test described herein and HPV-related HNSCC was studied by looking at how the markers described herein improve in patients whose tumors are positive for $p16^{INK4a}$. Fourteen oropharyngeal cancer subjects were evaluated. For each subject, the $p16^{INK4a}$ immunohistochemistry results from their tumor tissue and solCD44 and protein results from their oral rinses were obtained. Mean levels of solCD44 and protein level were lower in HPV$^+$ cases (CD44: 3.17 vs. 4.2, p=0.55, protein: 0.83 vs. 1.07, p=0.49) though differences did not reach statistical significance. The solCD44 and protein tests that were measured using the supernatants from oral rinses were combined with $p16^{INK4a}$ levels detected using the pellets from the same oral rinses.

An in vitro assay was performed for the quantitative determination of human $p16^{INK4a}$ protein in lysed samples from the oral rinse pellets. Sample pellets were placed in 200 µL of cell lysis buffer (SIGMA) containing protease inhibitor (Thermo Scientific) for stabilization of solubilized $p16^{INK4a}$. Then samples were heated at 95° C. for 10 minutes, which facilitates complete lysis of cells for better detection of $p16^{INK4a}$. The $p16^{INK4a}$ protein was quantified using a colorimetric ELISA sandwich technique using microtiter strips coated with the $p16^{INK4a}$-specific, monoclonal antibody E6H4™ (Roche mtm laboratories AG) and a second $p16^{INK4a}$-specific, monoclonal antibody labeled with HRP. Quantitation was performed by generating a standard curve based on known $p16^{INK4a}$ levels (Standards 1-6). The levels in test samples were determined by interpolation based on the standard curve. A microtiter plate reader was used to measure absorbance in each well at a wavelength of 450 nm (reference wavelength: 620 nm). A calculation program based on the 4-parameter method was used to obtain the final $p16^{INK4a}$ sample concentrations. The results are stated in U/mL and study samples were measured in duplicates, each with a volume of 100 µL. A cut-off value of 15 U/mL was verified as the appropriate threshold to classify an individual clinical specimen as positive for the Cervatec™ $p16^{INK4a}$ ELISA (Roche mtm laboratories AG) result by a multicenter clinical study (Protocol #9502-06-REG-DE-001).

Using this combined method, $p16^{INK4a}$ in combination with CD44 and protein was tested in 14 HNSCC patients including patients with oral cavity or oropharyngeal squamous cell carcinoma (CA) or unknown primary carcinomas (UK1 CA). Three healthy volunteers (HV) were also tested (see Table 1). Two patients with low levels of CD44 (cut-off set at 2.7 ng/ml) and protein (cut-off set at 1.0 mg/ml) had $p16^{INK4a}$ levels above the cut-off of 15 U/ml. CD44 and protein also each identified tumors that were not detected by the other tests. Thus, the addition of $p16^{INK4a}$ to the panel improves sensitivity. The 3 healthy volunteers that were tested all had levels for each marker below the cut-offs.

TABLE 1

| N | Conc. U/ml* p16INK4a | Conc. ng/ml CD44 (x5) | Conc. mg/ml Protein | Sample | Group** | Gender | Age | Race | Ethnicity |
|---|---|---|---|---|---|---|---|---|---|
| 1 | 0 | 1.6 | 0.63 | 17 | UK 1 CA | Female | 47 | White | Hispanic |
| 2 | 3.099 | 4.19 | 0.398 | 79 | CA | Female | 65 | White | Non-Hispanic |
| 3 | 16.981 | 2.536 | 0.583 | 167 | CA | Female | 50 | White | Hispanic |
| 4 | 12.554 | 4.29 | 0.716 | 262 | UK 1 CA | Male | 56 | White | Non-Hispanic |
| 5 | 3.529 | 8.88 | 0.892 | 86 | CA | Male | 67 | White | Hispanic |
| 6 | 7.758 | 3.355 | 0.781 | 24 | UK 1 CA | Male | 66 | Black | Non-Hispanic |
| 7 | 0 | 1.645 | 1.054 | 221 | UK 1 CA | Male | 50 | White | Hispanic |
| 8 | 5.687 | 4 | 1.262 | 239 | UK 1 CA | Male | 58 | White | Hispanic |
| 9 | 0 | 10.325 | 1.309 | 273 | CA | Male | 46 | White | Non-Hispanic |
| 10 | 6.896 | 1.13 | 0.604 | 345 | CA | Male | 59 | White | Non-Hispanic |
| 11 | 5.123 | 0.93 | 0.472 | 367 | CA | Male | 58 | White | Non-Hispanic |
| 12 | 16.752 | 1.18 | 0.469 | 370 | CA | Male | 62 | White | Hispanic |
| 13 | 8.812 | 4.555 | 0.792 | 374 | CA | Male | 60 | White | Hispanic |
| 14 | 9.421 | 2.56 | 1.037 | 377 | CA | Female | 63 | White | Non-Hispanic |
| NL1 | 0 | 1.645 | 0.797 | UM001 | HV | Female | 41 | White | Non-Hispanic |
| NL2 | 0 | 1.295 | 0.329 | UM009 | HV | Female | 49 | White | Hispanic |
| NL3 | 0.141 | 0.545 | 0.378 | UM030 | HV | Female | 57 | Asian | Non-Hispanic |

*1 U/ml = 2.8 pg/ml of p16 INK4a protein.
**CA: Cancer, UK 1 CA: Unknown primary cancer, HV: Healthy volunteer Example 2

Using immunohistochemistry on oral cancer tissues, a panel of markers (CD44 and EGFR), which are associated with poor prognosis were evaluated. We determined the relationship between expression of CD44, EGFR, and p16 (the surrogate marker for HPV) in tissue with solCD44 and protein oral rinse levels.

TABLE 2

| Patient demographics and other characteristic | | |
|---|---|---|
| Variable | N | % |
| Age (yrs) | | |
| Mean (standard deviation) | 60.4 | (9.8) |
| Median (minimum-maximum) | 61 | (40-83) |
| Gender | | |
| Female | 6 | 16.2 |
| Male | 31 | 83.8 |
| Ethnicity | | |
| Hispanic | 22 | 59.5 |
| Non-Hispanic | 15 | 40.5 |
| Race | | |
| White | 29 | 78.4 |
| Black | 8 | 21.6 |
| Smoking | | |
| Never | 5 | 13.5 |
| Former | 8 | 21.6 |
| Current | 24 | 64.9 |
| Alcohol, past | | |
| Never | 8 | 22.2 |
| Mild(<3 drinks/day) | 10 | 27.8 |
| Heavy(>=3 drinks/day) | 18 | 50.0 |
| Missing | 1 | |
| Alcohol, current | | |
| None | 12 | 37.5 |
| Mild | 8 | 25.0 |
| Heavy | 12 | 37.5 |
| Missing | 5 | |
| HealthCare | | |
| Yes | 20 | 54.1 |
| No | 17 | 45.9 |
| Education | | |
| Grades 1-8 (Elementary) | 6 | 16.2 |
| Grades 9-11 (Some high school) | 5 | 13.5 |
| Grade 12 or GED (High school graduate) | 12 | 32.4 |

TABLE 2-continued

Patient demographics and other characteristic

| Variable | N | % |
|---|---|---|
| College 1-3 years (Some college/technical school) | 6 | 16.2 |
| College 4+ years (College graduate) | 8 | 21.6 |
| Employment | | |
| Employed for wages | 7 | 19.4 |
| Self-employed | 6 | 16.7 |
| Retired | 8 | 22.2 |
| Unable to work | 6 | 16.7 |
| Out-of-work for less than 1 year | 3 | 8.3 |
| Out-of-work for more than 1 year | 6 | 16.7 |
| Missing | 1 | |
| Income | | |
| Less than $10,000 | 16 | 57.1 |
| $10,000 to <$15,000 | 1 | 3.6 |
| $20,000 to <$25,000 | 2 | 7.1 |
| $25,000 to <$35,000 | 2 | 7.1 |
| $35,000 to <$50,000 | 2 | 7.1 |
| $50,000 to <$75,000 | 2 | 7.1 |
| $75,000 or more | 3 | 10.7 |
| Missing | 9 | |

TABLE 3

Disease characteristics, treatment, and outcome

| Variable | N | % |
|---|---|---|
| Disease | | |
| Lip and Oral cavity cancer | 13 | 35.1 |
| Oropharyngeal cancer | 24 | 64.9 |
| Stage | | |
| I | 3 | 8.11 |
| II | 1 | 2.7 |
| III | 8 | 21.6 |
| IV | 9 | 24.3 |
| IVA | 12 | 32.4 |
| IVB | 4 | 10.8 |
| T-stage | | |
| T1 | 5 | 13.5 |
| T2 | 5 | 13.5 |
| T3 | 11 | 29.7 |
| T4 | 4 | 10.8 |
| T4a | 10 | 27.0 |
| T4b | 2 | 5.4 |
| N-stage | | |
| Nx | 1 | 2.7 |
| N0 | 14 | 37.8 |
| N1 | 3 | 8.1 |
| N2a | 1 | 2.7 |
| N2b | 6 | 16.2 |
| N2c | 9 | 24.3 |
| N3 | 3 | 8.1 |
| M-stage | | |
| M0 | 33 | 89.2 |
| Mx | 4 | 10.8 |
| Treatment | | |
| Chemo/RT | 16 | 43.2 |
| Surgery/Chemo/RT | 9 | 24.3 |
| Surgery | 5 | 13.5 |
| Surgery/RT | 2 | 5.4 |
| Surgery/Chemo | 1 | 2.7 |
| Chemo | 1 | 2.7 |
| None/Missing | 2 | 5.4 |
| Pathology | | |
| Biopsy | 25 | 67.6 |
| Surgical Resection (all negative margins) | 12 | 32.4 |
| Lymphovascular | | |
| Yes | 2 | 16.7 |
| No | 10 | 83.3 |
| Missing | 25 | |
| Perineural | | |
| Yes | 3 | 25.0 |
| No | 9 | 75.0 |
| Missing | 25 | |
| Differentiation (Velos) | | |
| Well | 6 | 18.8 |
| Moderate | 17 | 53.1 |
| Moderate-Poor | 2 | 6.3 |
| Poor | 7 | 21.9 |
| Missing | 5 | |
| Invasion (Velos) | | |
| Yes (., 5, 10, 15, 22 mm) | 5 | 17.2 |
| No | 24 | 82.8 |
| Missing | 8 | |
| Outcome | | |
| Progression/Recurrence | 21 | 56.8 |
| Event-free | 16 | 43.2 |
| Status | | |
| Dead | 16 | 43.2 |
| Alive | 21 | 56.8 |

TABLE 4

CD44, Log2 CD44, and protein in oral rinses by IHC variables, PD status and vital status

| | CD44 | | | | | log2CD44 | | | | | Protein | | | | |
|---|---|---|---|---|---|---|---|---|---|---|---|---|---|---|---|
| | N | Mean | SD | SE | P | N | Mean | SD | SE | P | N | Mean | SD | SE | P |
| All | 36 | 7.91 | 10.85 | 1.81 | | 36 | 2.35 | 1.20 | 0.20 | | 36 | 1.03 | 0.58 | 0.10 | |
| p16 | | | | | | | | | | | | | | | |
| Positive | 16 | 9.15 | 14.32 | 3.58 | 0.578 | 16 | 2.47 | 1.26 | 0.31 | 0.603 | 16 | 1.10 | 0.64 | 0.16 | 0.557 |
| Negative | 20 | 6.92 | 7.25 | 1.62 | | 20 | 2.26 | 1.18 | 0.26 | | 20 | 0.98 | 0.53 | 0.12 | |
| P16 new definition | | | | | | | | | | | | | | | |
| Nuclear/ Nuclear + cyt | 14 | 6.06 | 4.34 | 1.16 | 0.335 | 14 | 2.29 | 0.97 | 0.26 | 0.811 | 14 | 1.12 | 0.61 | 0.16 | 0.474 |

TABLE 4-continued

CD44, Log2 CD44, and protein in oral rinses by IHC variables, PD status and vital status

| | CD44 | | | | | log2CD44 | | | | | Protein | | | | |
|---|---|---|---|---|---|---|---|---|---|---|---|---|---|---|---|
| | N | Mean | SD | SE | P | N | Mean | SD | SE | P | N | Mean | SD | SE | P |
| Cyt only/ No stain | 22 | 9.09 | 13.45 | 2.87 | | 22 | 2.39 | 1.35 | 0.29 | | 22 | 0.98 | 0.57 | 0.12 | |
| CD44 | | | | | | | | | | | | | | | |
| Membrane | 22 | 9.26 | 13.42 | 2.86 | | 22 | 2.45 | 1.31 | 0.28 | | 22 | 1.05 | 0.64 | 0.14 | |
| Cytoplasmic | 2 | 10.69 | 6.52 | 4.61 | | 2 | 3.27 | 0.94 | 0.67 | | 2 | 1.30 | 0.70 | 0.49 | |
| M and C | 2 | 3.53 | 3.06 | 2.17 | | 2 | 1.48 | 1.46 | 1.03 | | 2 | 0.62 | 0.34 | 0.24 | |
| No stain | 10 | 5.27 | 3.66 | 1.16 | | 10 | 2.13 | 0.91 | 0.29 | | 10 | 1.04 | 0.48 | 0.15 | |
| CD44 stain | 26 | 8.93 | 12.49 | 2.45 | 0.186 | 26 | 2.44 | 1.30 | 0.26 | 0.506 | 26 | 1.03 | 0.62 | 0.12 | 0.986 |
| No stain | 10 | 5.27 | 3.66 | 1.16 | | 10 | 2.13 | 0.91 | 0.29 | | 10 | 1.04 | 0.48 | 0.15 | |
| Membrane only, universal | 21 | 9.58 | 13.67 | 2.98 | | 21 | 2.50 | 1.32 | 0.29 | | 21 | 1.05 | 0.65 | 0.14 | |
| Other | 5 | 6.20 | 5.47 | 2.45 | | 5 | 2.17 | 1.33 | 0.59 | | 5 | 0.94 | 0.52 | 0.23 | |
| No stain | 10 | 5.27 | 3.66 | 1.16 | | 10 | 2.13 | 0.91 | 0.29 | | 10 | 1.04 | 0.48 | 0.15 | |
| Memb_only, universal | 21 | 9.58 | 13.67 | 2.98 | 0.219 | 21 | 2.50 | 1.32 | 0.29 | 0.392 | 21 | 1.05 | 0.65 | 0.14 | 0.804 |
| Other/No stain | 15 | 5.58 | 4.17 | 1.08 | | 15 | 2.15 | 1.02 | 0.26 | | 15 | 1.00 | 0.48 | 0.12 | |
| EGFR | | | | | | | | | | | | | | | |
| Membrane | 3 | 3.55 | 1.83 | 1.06 | | 3 | 1.68 | 0.83 | 0.48 | | 3 | 1.31 | 0.85 | 0.49 | |
| Cytoplasmic | 8 | 12.32 | 20.05 | 7.09 | | 8 | 2.59 | 1.62 | 0.57 | | 8 | 1.25 | 0.71 | 0.25 | |
| M and C | 21 | 7.68 | 7.07 | 1.54 | | 21 | 2.49 | 1.10 | 0.24 | | 21 | 0.98 | 0.51 | 0.11 | |
| No stain | 4 | 3.57 | 1.84 | 0.92 | | 4 | 1.66 | 0.88 | 0.44 | | 4 | 0.67 | 0.31 | 0.15 | |
| EGFR stain | 32 | 8.46 | 11.39 | 2.01 | 0.035 | 32 | 2.44 | 1.22 | 0.22 | 0.223 | 32 | 1.08 | 0.59 | 0.10 | 0.186 |
| No stain | 4 | 3.57 | 1.84 | 0.92 | | 4 | 1.66 | 0.88 | 0.44 | | 4 | 0.67 | 0.31 | 0.15 | |
| Mem & Cyt, universal | 19 | 6.90 | 6.10 | 1.40 | | 19 | 2.39 | 1.03 | 0.24 | | 19 | 0.94 | 0.51 | 0.12 | |
| Other | 13 | 10.73 | 16.44 | 4.56 | | 13 | 2.51 | 1.49 | 0.41 | | 13 | 1.28 | 0.66 | 0.18 | |
| No stain | 4 | 3.57 | 1.84 | 0.92 | | 4 | 1.66 | 0.88 | 0.44 | | 4 | 0.67 | 0.31 | 0.15 | |
| Memb & Cyt, universal | 19 | 6.90 | 6.10 | 1.40 | 0.579 | 19 | 2.39 | 1.03 | 0.24 | 0.850 | 19 | 0.94 | 0.51 | 0.12 | 0.314 |
| Other/No stain | 17 | 9.04 | 14.60 | 3.54 | | 17 | 2.31 | 1.40 | 0.34 | | 17 | 1.14 | 0.64 | 0.16 | |
| Keratinization | 14 | 10.37 | 15.97 | 4.27 | 0.284 | 14 | 2.46 | 1.49 | 0.40 | 0.681 | 14 | 1.04 | 0.67 | 0.18 | 0.949 |
| Non-keratinization | 22 | 6.35 | 5.62 | 1.20 | | 22 | 2.29 | 1.01 | 0.21 | | 22 | 1.03 | 0.53 | 0.11 | |
| PD (Progressive Disease) | 21 | 10.80 | 13.61 | 2.97 | 0.043 | 21 | 2.67 | 1.46 | 0.32 | 0.068 | 21 | 1.19 | 0.71 | 0.15 | 0.030 |
| No PD | 16 | 4.34 | 1.74 | 0.43 | | 16 | 2.01 | 0.59 | 0.15 | | 16 | 0.82 | 0.18 | 0.04 | |

TABLE 4-continued

CD44, Log2 CD44, and protein in oral rinses by IHC variables, PD status and vital status

| | CD44 | | | | | log2CD44 | | | | | Protein | | | | |
|---|---|---|---|---|---|---|---|---|---|---|---|---|---|---|---|
| | N | Mean | SD | SE | P | N | Mean | SD | SE | P | N | Mean | SD | SE | P |
| Dead | 16 | 11.17 | 14.75 | 3.69 | 0.118 | 16 | 2.74 | 1.41 | 0.35 | 0.118 | 16 | 1.26 | 0.72 | 0.18 | 0.050 |
| Alive | 21 | 5.60 | 5.40 | 1.18 | | 21 | 2.11 | 0.96 | 0.21 | | 21 | 0.86 | 0.35 | 0.08 | |

CD44 in ng/ml(x5) and protein in mg/ml.
SD: standard deviation,
SE: standard error.
P: P-value from Student t-test.

Nuclear staining with p16 is an effective indicator of HPV infection. SolCD44 levels are higher in HPV$^-$ than HPV$^+$.

TABLE 5

Univariate effects of potentially prognostic factors on PFS and OS

| | PFS | | OS | |
|---|---|---|---|---|
| Prognostic factor | HR (95% CI) | P-value | HR (95% CI) | P-value |
| Log 2 CD44 1-unit increase | 1.407 (0.989, 2.001) | 0.0574 | 1.638 (1.081, 2.482) | 0.0200 |
| Protein 1-unit increase | 3.607 (1.626, 7.999) | 0.0016 | 3.987 (1.701, 8.928) | 0.0013 |
| CD44 >= 10 v. <10 | 3.180 (1.306, 7.742) | 0.0108 | 4.595 (1.601, 13.186) | 0.0046 |
| Protein >= 1 v. <1 | 3.243 (1.349, 7.798) | 0.0086 | 3.379 (1.239, 9.214) | 0.0173 |
| Smoking: current v. no | 0.911 (0.155, 4.993) | 0.9148 | 3.099 (0.346, 27.738) | 0.3117 |
| Smoking: former v. no | 1.410 (0.321, 6.198) | 0.6496 | 2.750 (0.355, 21.328) | 0.3331 |
| Smoking: current v. no/former | 1.501 (0.575, 3.915) | 0.4069 | 1.261 (0.436, 3.642) | 0.6688 |
| Alcohol: heavy v. no/slight | 2.236 (0.919, 5.439) | 0.0759 | 2.775 (0.959, 8.031) | 0.0598 |
| P16$^+$ v. p16$^-$ | 0.674 (0.268, 1.693) | 0.4014 | 0.748 (0.265, 2.113) | 0.5831 |
| P16 Nuclear vs. cyst only/no stain | 0.628 (0.240, 1.640) | 0.3420 | 0.765 (0.261, 2.242) | 0.6251 |
| CD44: memb_only, universal v. other | 1.763 (0.698, 4.452) | 0.2304 | 2.407 (0.765, 7.579) | 0.1333 |
| EGFR: memb & cyt, universal v. other | 1.691 (0.686, 4.173) | 0.2539 | 1.203 (0.427, 2.289) | 0.7269 |
| Stage IV v. I-III | 2.994 (1.005, 8.921) | 0.0490 | 2.824 (0.802, 9.939) | 0.1059 |
| Stage III-IV v. I-II | 2.732 (0.367, 20.355) | 0.3268 | 2.164 (0.285, 16.415) | 0.4552 |
| T4- v. T1-3 | 3.055 (1.260, 7.408) | 0.0135 | 2.973 (1.078, 8.204) | 0.0353 |
| Black v. White | 5.432 (2.152, 13.714) | 0.0003 | 6.530 (2.286, 18.658) | 0.0005 |
| Non-Hispanic v. Hispanic | 3.001 (1.254, 7.182) | 0.0136 | 4.009 (1.431, 11.234) | 0.0083 |
| Gender: female v. male | 2.388 (0.924, 6.170) | 0.0723 | 1.770 (0.494, 6.338) | 0.3801 |
| Age 1-unit increase | 1..003 (0.961, 1.047) | 0.8778 | 1.043 (0.991, 1.096) | 0.1046 |

HR (95% CI): estimated hazard ratio and corresponding 95% confidence interval from univariate Cox models.

Blocked section in Table 5 shows significant associations between marker levels and prognostic variables.

TABLE 6

Bivariate Cox regression models

| | PFS | | OS | |
|---|---|---|---|---|
| Prognostic factor | HR (95% CI) | P-value | HR (95% CI) | P-value |
| CD44 >=10 v. <10 | 2.327 (0.891, 6.078) | 0.0847 | 4.370 (1.489, 12.824) | 0.0073 |
| Stage IV v. I-III | 2.197 (0.675, 7.148) | 0.1910 | 1.487 (0.188, 11.784) | 0.7073 |
| CD44 >=10 v. <10 | 2.949 (1.195, 7.281) | 0.0190 | 3.610 (1.164, 11.194) | 0.0262 |
| Stage III-IV v. I-II | 2.014 (0.262, 15.498) | 0.5014 | 1.894 (0.488, 7.348) | 0.3558 |
| Protein >=1 v. <1 | 2.470 (0.956, 6.381) | 0.0619 | 2.710 (0.921, 7.974) | 0.0702 |
| Stage IV v. I-III | 2.059 (0.630, 6.734) | 0.2321 | 1.886 (0.486, 7.319) | 0.3589 |
| Protein >=1 v. <1 | 3.018 (1.223, 7.446) | 0.0165 | 3.256 (1.139, 9.305) | 0.0276 |
| Stage III-IV v. I-II | 1.728 (0.219, 13.667) | 0.6040 | 1.260 (0.151, 10.506) | 0.8312 |

The effect of solCD44 and total protein in predicting progression free survival (PFS) and overall survival (OS) appears to be independent of stage.

Example 3

Figure 2A:
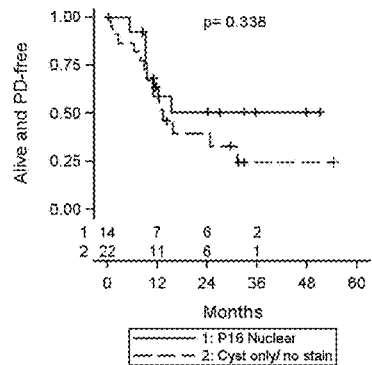
FIGS. 2A to 2RR are graphs showing PFS (FIGS. 2A, 2C, 2E, 2G, 2I, 2K, 2M, 2O, 2Q, 2S, 2U, 2W, 2Y, 2AA, 2CC, 2EE, 2GG, 2II, 2KK, 2MM, 2OO, 2QQ) and OS (FIGS. 2B, 2D, 2F, 2H, 2J, 2L, 2N, 2P, 2R, 2T, 2V, 2X, 2Z, 2BB, 2DD, 2FF, 2HH, 2JJ, 2LL, 2NN, 2PP, 2RR) in subjects characterized as p16 nuclear vs. cytoplasmic/no stain (FIGS. 2A-2B), p16$^+$ vs. p16$^-$ staining (FIGS. 2C-2D), solCD44≥10 ng/ml vs. <10 ng/ml (FIGS. 2E-2F), total protein <1 mg/ml vs. ≥1 mg/ml (FIGS. 2G-2H), CD44 staining vs. no staining (FIGS. 2I-2J), CD44 membrane only/universal staining vs. no staining/other (FIGS. 2K-2L), EGFR membrane and cytoplasmic staining vs. no staining/other (FIGS. 2M-2N), EGFR membrane and cytoplasmic vs. other vs. no stain (FIGS. 2O-2P), EGFR membrane v. cytoplasmic/no stain (FIGS. 2Q-2R), EGFR membrane v. cytoplasmic only vs. no stain (FIGS. 2S-2T), keratinizing vs. non-keratinizing (FIGS. 2U-2V), current smoker vs. no/former smoker (FIGS. 2W-2X), no alcohol vs. light/moderate alcohol v. heavy alcohol exposure (FIGS. 2Y-2Z), heavy vs. slight/no alcohol exposure (FIGS. 2AA-2BB), lip and oral cavity cancer vs. oropharyngeal cancer (FIGS. 2CC-2DD), stage I/II vs. stage III/IV cancer (FIGS. 2EE-2FF), stage I/II/III vs. stage IV cancer (FIGS. 2GG-2HH), T1-T3 vs. T4 cancer (FIGS. 2II-2JJ), N0 vs. N1-N3, Nx (FIGS. 2KK-2LL), female vs. male (FIGS. 2MM-2NN), White vs. Black (FIGS. 2OO-2PP), or Hispanic vs. non-Hispanic (FIGS. 2QQ-2RR).
Figure 2B:
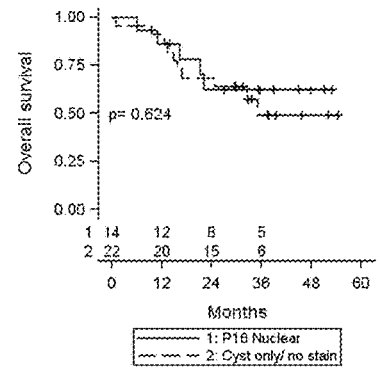
Figure 2C:
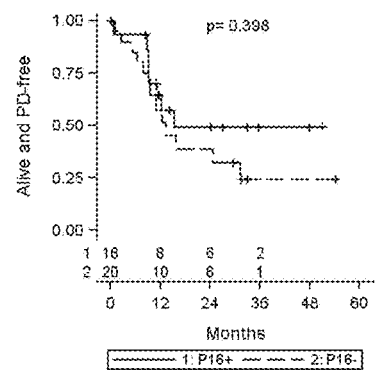
Figure 2D:
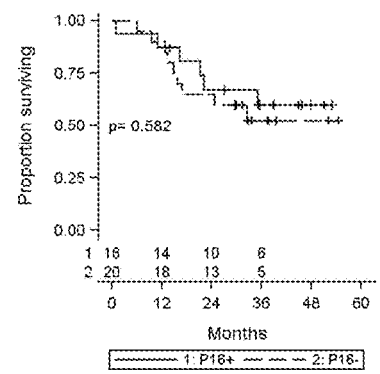
Figure 2E:
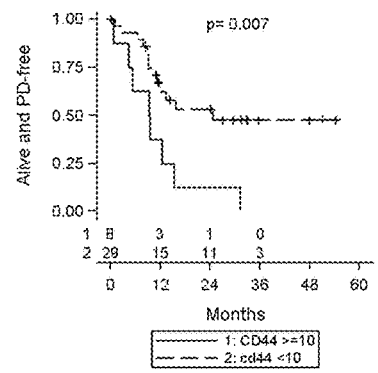
Figure 2F:
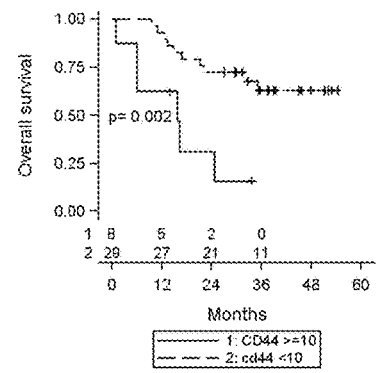
Figure 2G:
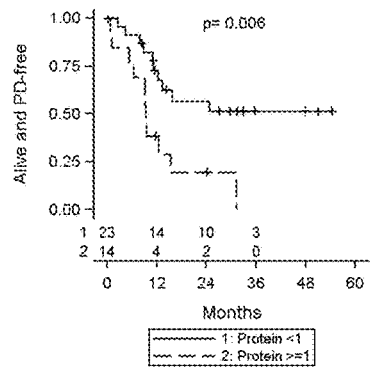
Figure 2H:
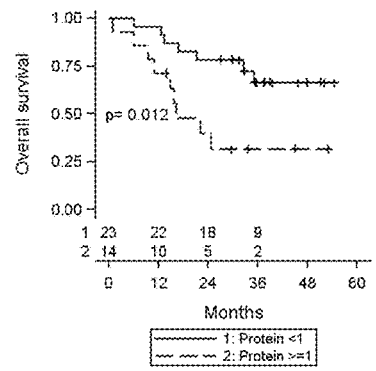
Figure 2I:
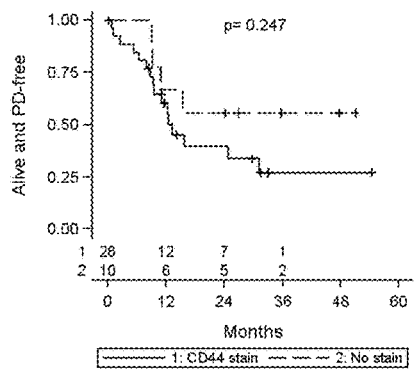
Figure 2J:
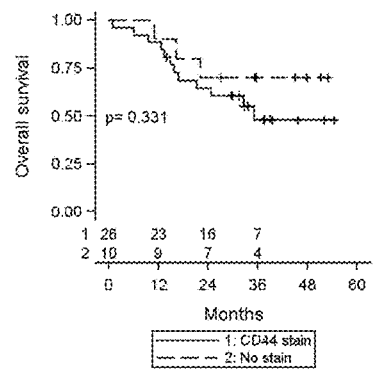
Figure 2K:
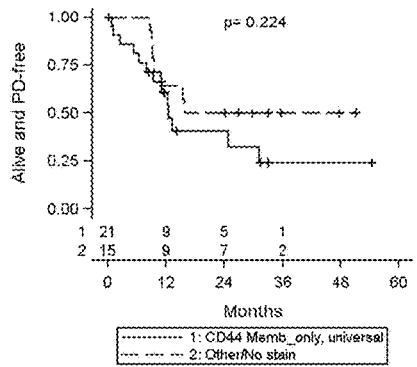
Figure 2L:
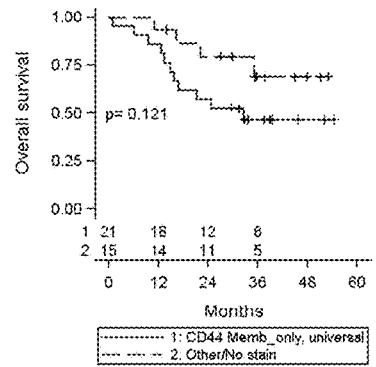
Figure 2M:
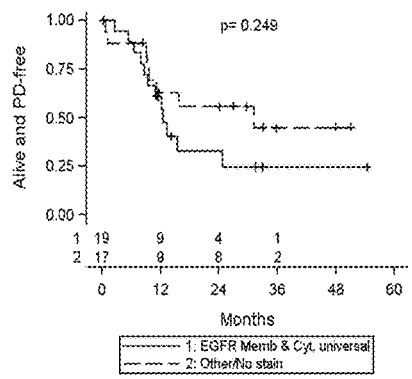
Figure 2N:
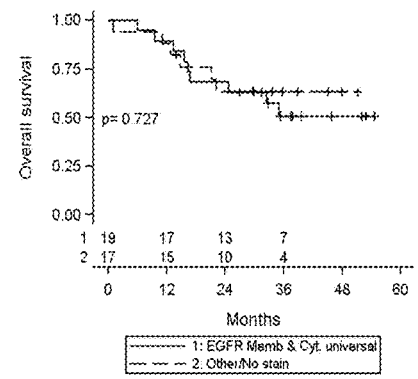
Figure 2O:
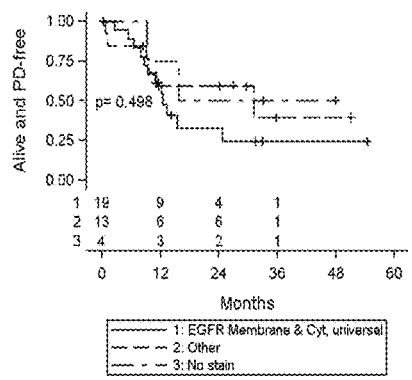
Figure 2P:
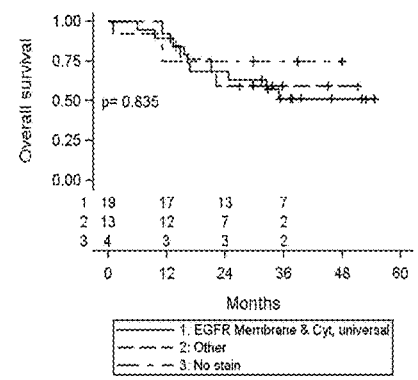
Figure 2Q:
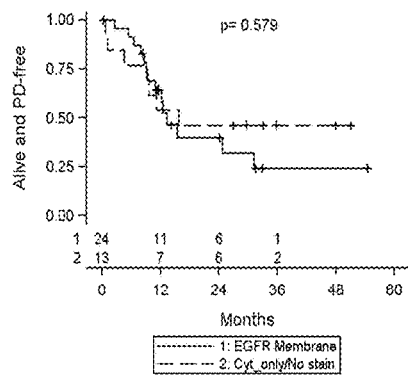
Figure 2R:
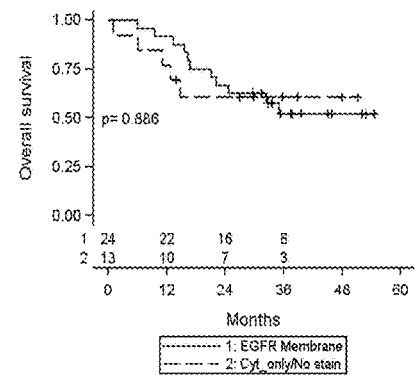
Figure 2S:
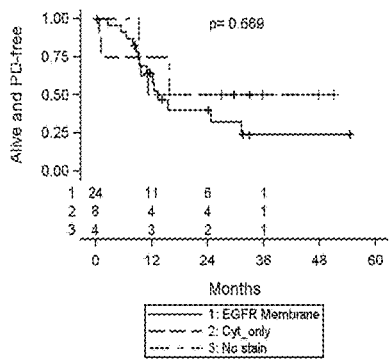
Figure 2T:
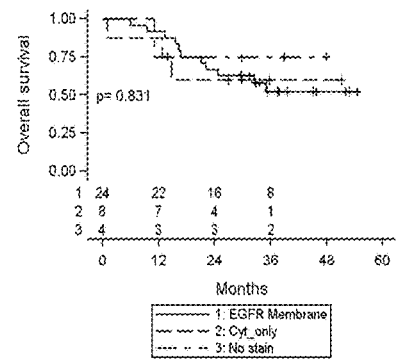
Figure 2U:
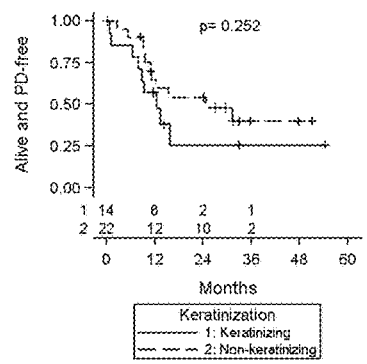
Figure 2V:
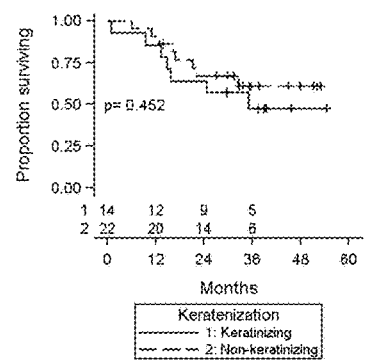
Figure 2W:
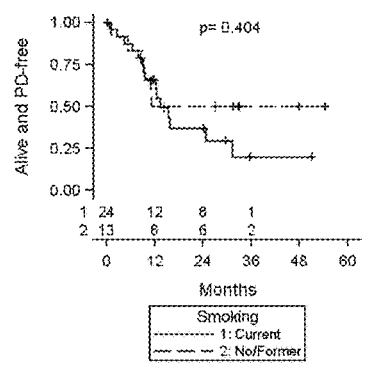
Figure 2X:
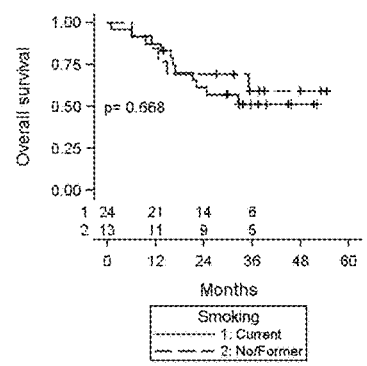
Figure 2Y:
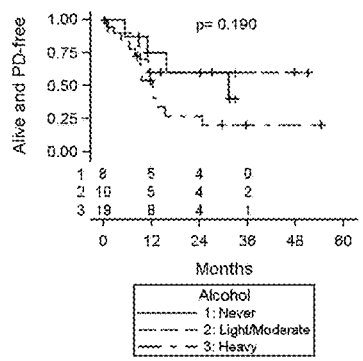
Figure 2Z:
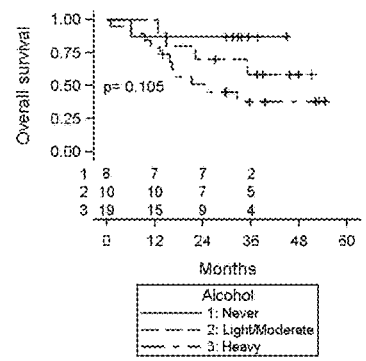
Figure 2A:
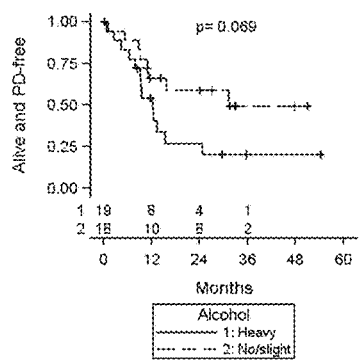
Figure 2B:
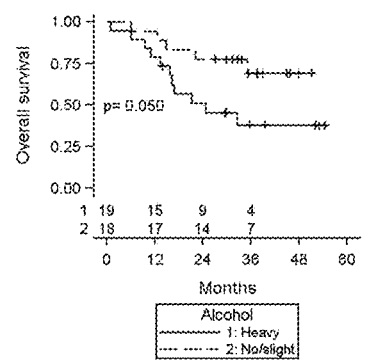
Figure 2C:
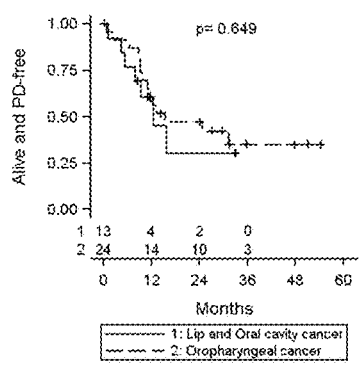
Figure 2D:
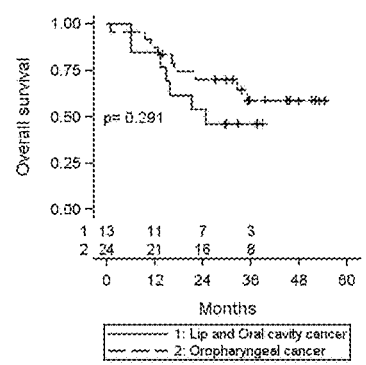
Figure 2E:
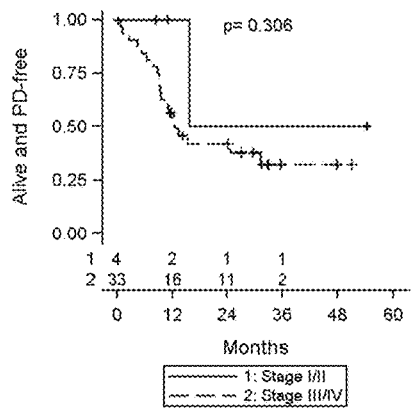
Figure 2F:
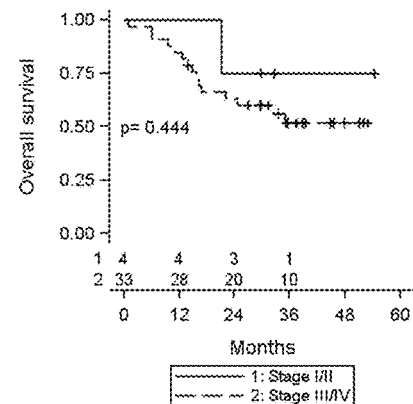
Figure 2G:
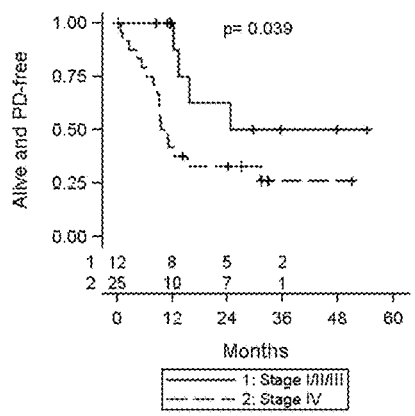
Figure 2H:
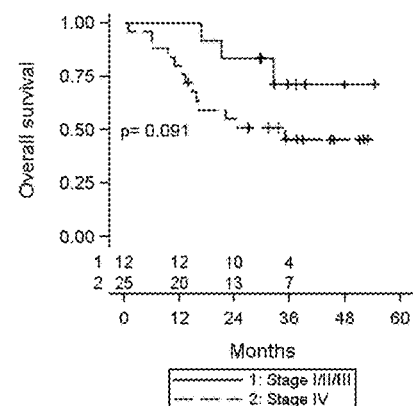
Figure 2I:
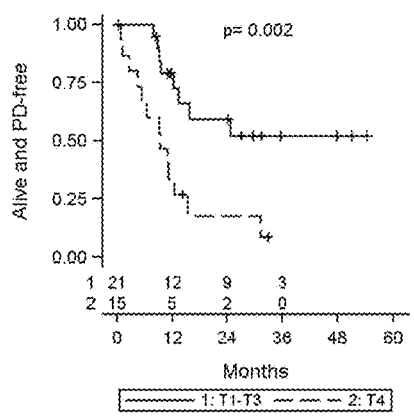
Figure 2J:
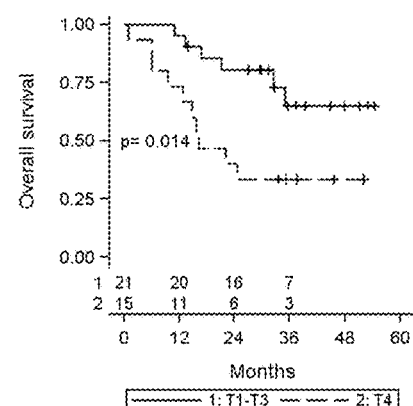
Figure 2K:
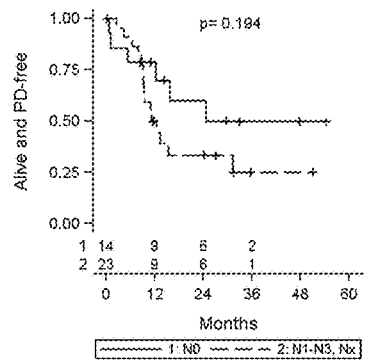
Figure 2L:
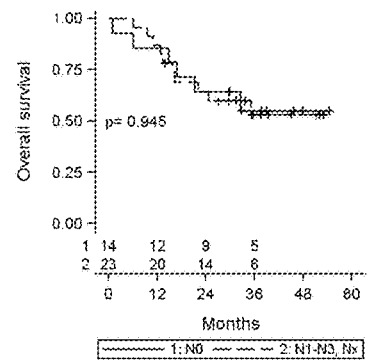
Figure 2M:
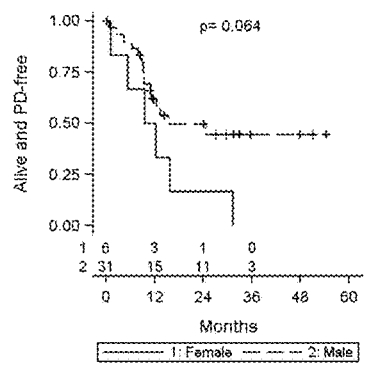
Figure 2N:
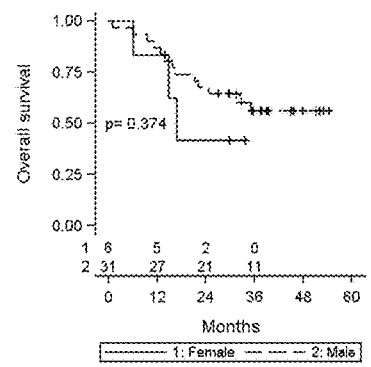
Figure 2O:
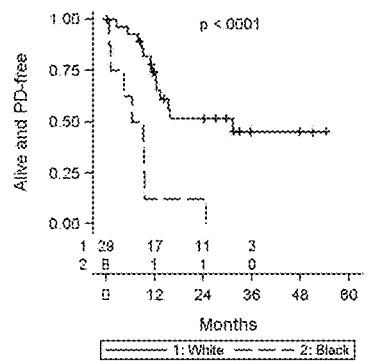
Figure 2P:
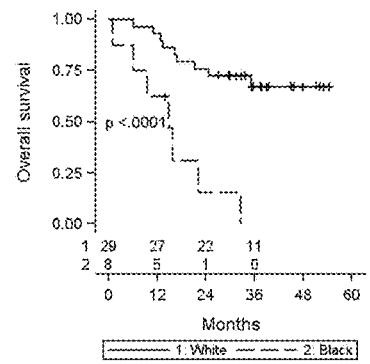
Figure 2Q:
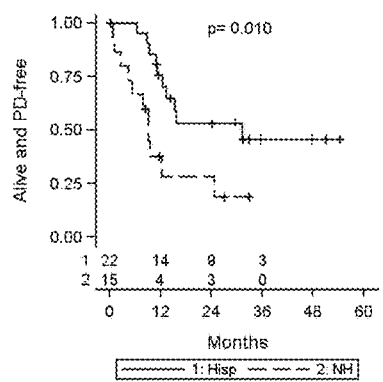
Figure 2R:
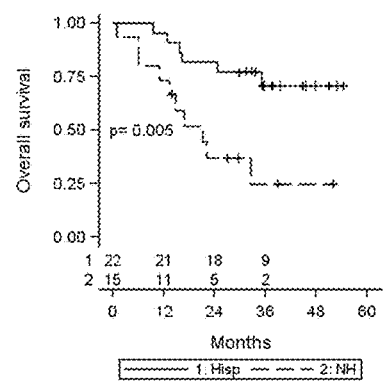
Figure 3A:
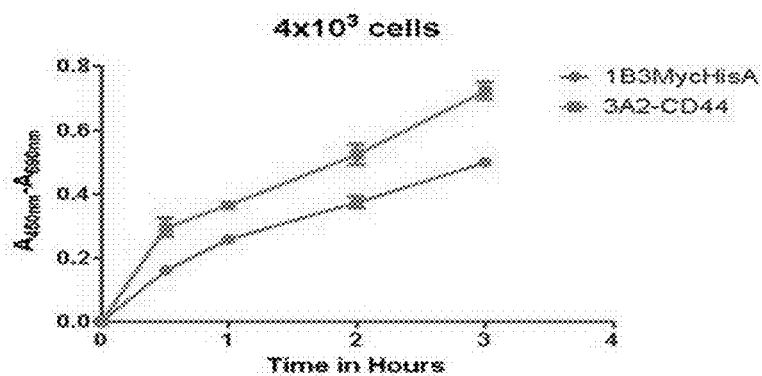
FIGS. 3A-3C are graphs showing that CD44 overexpression increased proliferation (FIG. 3A), migration (FIG. 3B), and cisplatin resistance (FIG. 3C).
Figure 3B:
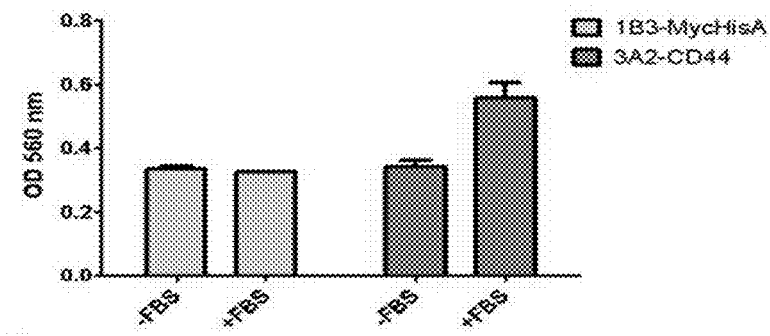
Figure 3C:
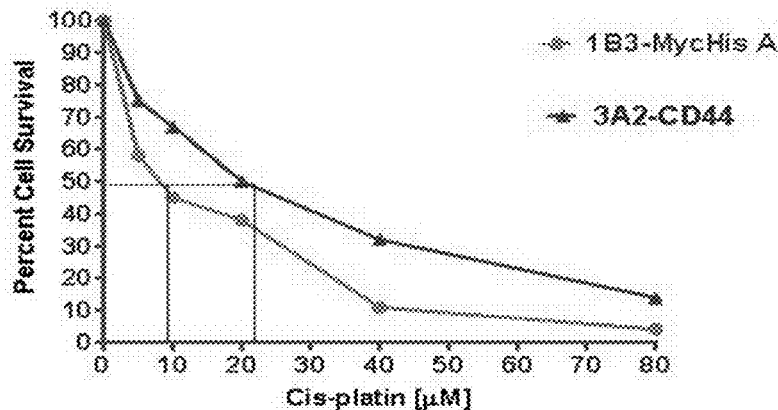
Figure 4A:
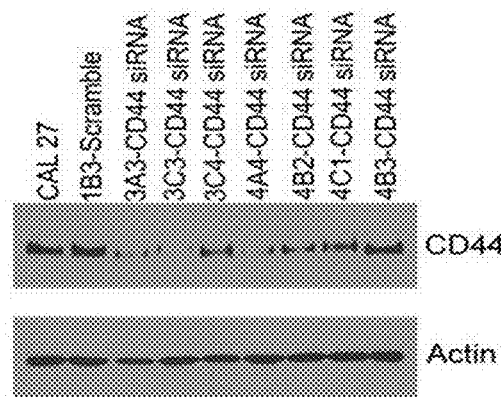
FIG. 4A is a Western blot from stable clones with down-regulated CD44.
Figure 4B:
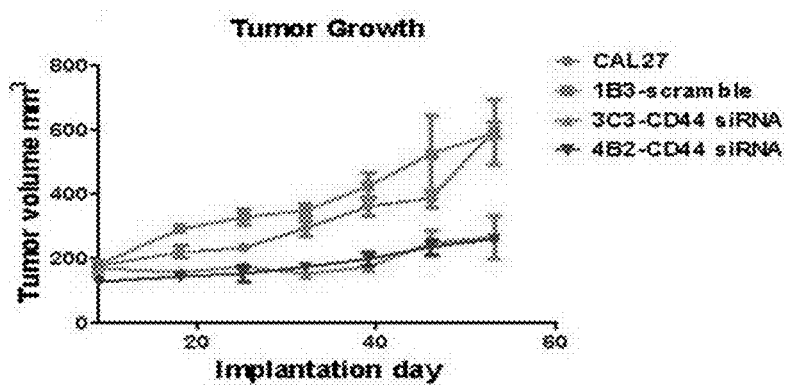
FIG. 4B is a graph showing tumor growth inhibition in nude mice for two of the CD44siRNA clones compared to scramble or wild type CAL 27.
Figure 5:
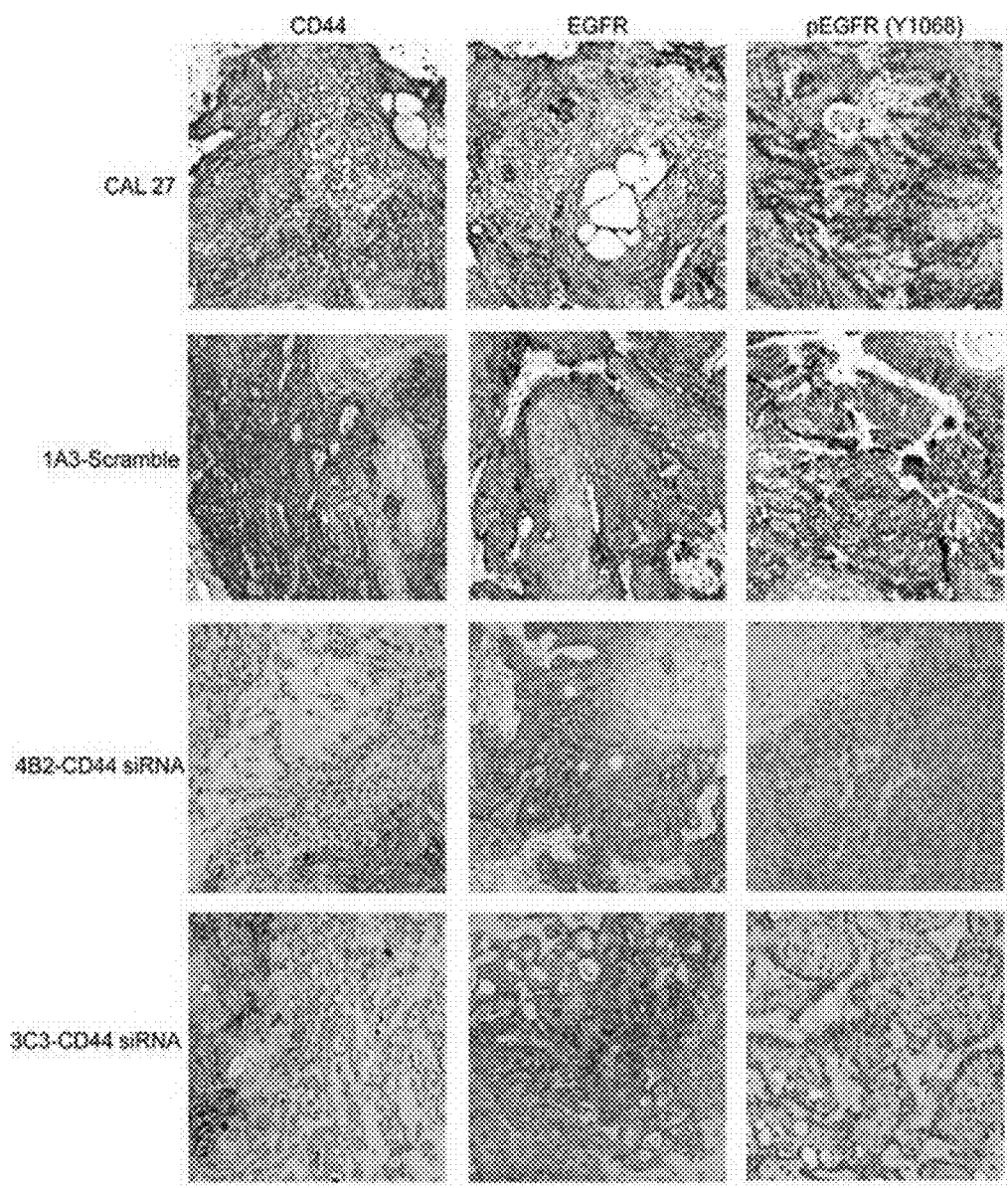
FIG. 5 contains histology slides showing CD44, EGFR, and pEGFR (Y1068) staining in CAL 27 xenografts after treatment with CD44 siRNA or a scrambled sequence. CD44 downregulation inhibits EGFR expression and its phosphorylation (Y1068) in CAL 27 xenografts.

There is a tremendous need for a simple, inexpensive, noninvasive early detection test for HNSCC. Prior efforts have focused on CD44, a transmembrane glycoprotein that is emerging as a critical HNSCC tumor initiation marker. When SCC-25 cells (CD44 low) were transfected with CD44 standard form, it was shown that overexpression of CD44 resulted in increased proliferation, migration and cisplatin resistance (FIGS. 3A, 3B, 3C). In addition, knockdown of CD44 using the CD44 and EGFR high cell line CAL27 results in greatly diminished tumor growth in nude mice (FIG. 4A, 2B) (P<0.05). CD44 interacts has been shown to interact with key tyrosine kinases such as EGFR (the target for cetuximab therapy) to induce growth and migration. The disclosed data in FIG. 5 shows that total EGFR and its phosphorylated form (Y1068) are reduced on CD44-siRNA xenografts indicating that the two molecules are functionally related.

Because of the critical need for an early detection test and knowledge that CD44 could be cleaved to a soluble form, solCD44 was evaluated in oral rinses from cancer patients and controls. In a pilot study including 26 HNSCC patients and 10 healthy volunteers, it was shown that solCD44 could be detected in oral rinses and could distinguish patients with invasive disease from normal volunteers with a sensitivity of 79% and 100% specificity. To determine whether this test would work in a higher risk population, a control cohort with a history of tobacco and/or alcohol use and benign disease of the head and neck was developed. In this study with 102 HNSCC and 69 controls, the solCD44 ELISA test was shown to have a sensitivity of 62% and specificity of 88% and benign disease was shown not to significantly impact results. Levels of the markers were determined to be lower in subjects with laryngeal/hypopharyngeal tumors which are less frequent and located more distally in the upper aerodigestive tract (UADT).

To improve sensitivity, additional markers were examined Total protein, measured by a simple Lowry-like assay and originally used as a normalizer for hydration status, was found to be elevated in HNSCC compared to controls. When the same cohort were evaluated, it was shown for the first time that solCD44 and total protein levels combined, are more effective at distinguishing HNSCC from controls than either marker alone. More recent work in a cohort of 39 controls and 40 cases demonstrated that including other risk variables such as teeth loss and education improves the test, resulting in an area under the curve (AUC) for the multivariate analysis of 0.85.

TABLE 8

SolCD44, log2solCD44 and protein levels in oral rinses

| | | Cancer (N = 132) | | | Cancer (N = 124) | | | |
|---|---|---|---|---|---|---|---|---|
| | N | Mean | SD | SE | Mean | SD | SE | P-value |
| CD44 | 132 | 5.83 | 7.19 | 0.63 | 2.95 | 1.92 | 0.17 | <.0001 |
| Log2 CD44 | 132 | 2.01 | 1.16 | 0.10 | 1.30 | 0.87 | 0.08 | <.0001 |
| Protein | 132 | 0.98 | 0.55 | 0.05 | 0.77 | 0.41 | 0.04 | <.001 |

This study used a case-control design to evaluate soluble markers for HNSCC in 150 oropharyngeal and oral cavity HNSCC patients and 150 controls frequency matched for important variables. Table 7 shows an interim analysis of solCD44, log 2 SolCD44 and total protein levels in 132 cases and 124 controls. Cases and controls were successfully frequency matched for age, gender, race and ethnicity (p>0.5). Both solCD44 and total protein levels are significantly elevated. The logistic models in Table 8 are all adjusted for age. The test detected oral cancer best in black males. For black females, the sample size was smaller. There was no significant effect of markers either individually or together, however the corresponding odds ratios were in the same direction as black males. Among white males, the effect of log 2 CD44 was significant by itself or when protein was added. There was a slight improvement for model 3 compared to model 1. Finally, among white females, the markers were least effective, with AUCs near 0.60. Since the marker test worked best in black men, a group where HPV infection is less common, HPV expression was examined in the oral cancer cases.

Thirty-seven cases were identified with available FFPE tissue. Except for one patient with follow-up of 13.9 months, all remaining 20 alive patients had follow up in the range 27 to 54.4 months (median 37 months). Fourteen out of 16 deaths occurred within the first 2 years of follow-up. solCD44 and total protein levels were evaluated in oral rinses, and various staining patterns of CD44, EGFR and p16 (as a surrogate for HPV infection) were examined using IHC. Associations with progression-free and overall survival were also determined Important demographic and risk factor behaviors such as gender, race, ethnicity, tobacco and alcohol use were also evaluated. This cohort had the following demographics: mean age was 60.4 years, 16.2% were female, 59.5% were Hispanic, 21.6% were black, 64.9%

TABLE 7

Logistic models adjusted for age

| Group | Cases | Controls | Model | Variables | OR | p | AUC |
|---|---|---|---|---|---|---|---|
| Black Male | 15 | 15 | 1 | Log2 CD44 | 2.878 | 0.0457 | 0.853 |
| | | | 2 | Protein | 13.378 | 0.0250 | 0.862 |
| | | | 3 | Log2 CD44 | 2.078 | 0.2405 | 0.889 |
| | | | | & Protein | 5.450 | 0.1582 | |
| White Female | 90 | 76 | 1 | Log2 CD44 | 2.410 | <.0001 | 0.723 |
| | | | 2 | Protein | 2.101 | 0.0594 | 0.609 |
| | | | 3 | Log2 CD44 | 2.965 | <.0001 | 0.739 |
| | | | | & Protein | 0.468 | 0.1768 | |
| Black Female | 7 | 17 | 1 | Log2 CD44 | 1.963 | 0.2204 | 0.647 |
| | | | 2 | Protein | 3.796 | 0.2238 | 0.672 |
| | | | 3 | Log2 CD44 | 1.554 | 0.6705 | 0.689 |
| | | | | & Protein | 1.747 | 0.7916 | |
| White Female | 19 | 14 | 1 | Log2 CD44 | 1.262 | 0.6988 | 0.600 |
| | | | 2 | Protein | 1.896 | 0.3557 | 0.594 |
| | | | 3 | Log2 CD44 | 0.989 | 0.9823 | 0.594 |
| | | | | & Protein | 1.919 | 0.5364 | | were current smokers, 50% were heavy drinkers, 57.1% had income less than $10,000 per year. The group's disease characteristics were as follows: 35.1% were oral cavity (OC) and the remainder were oropharyngeal cancers (OP); only 32.4% of subjects were stage III or lower; patients were treated with chemoradiotherapy (43.2%), surgery and chemoradiotherapy (24.3%), surgery alone (13.5%), surgery plus radiation (5.4%), surgery and chemotherapy (2.7%), chemotherapy alone (2.7%) and nothing or the data was missing (5.4%). Nearly 57% recurred or progressed and 43.2% died.

Forty-four percent of tumors were p16+ as defined by 50% or more of the tumor cells staining positive for p16. Comparison of IHC patterns revealed that positive p16 staining, lack of CD44 membrane staining, lack of EGFR membrane and cytoplasmic staining pattern, and nonkeratinizing tumors were significantly associated with OP compared to OC tumors. There were no differences in staging or outcomes by tumor site. With respect to location of staining, p16 positivity was significantly associated with nuclear or nuclear and cytoplasmic p16 staining (p<0001) as opposed to only cytoplasmic staining or no staining. Similarly lack of universal CD44 membrane staining (p<0.0001) was associated with p16 positivity. Lack of universal EGFR membrane and cytoplasmic staining in the p16 positive tumors also reached statistical significance (p=0.02). Keratinization, gender, ethnicity, race, smoking and alcohol use were not significantly related to p16 positivity in this study.

SolCD44 and total protein oral rinse levels showed no significant differences based on p16 status whether the definition of p16+ as 1) 50% or more tumor cells p16+ or 2) any nuclear p16 staining as opposed to only cytoplasmic/no staining was used. However, for both solCD44 and total protein, significantly higher levels were associated with recurrence or progression (CD44:10.8 vs. 4.3 p=0.043, protein 1.2 vs. 0.8 p=0.030). Based on Kaplan-Meier, logrank test, and Cox regression analysis, significant predictors of progression free survival were CD44 ($\geq$10 v. <10, HR=3.18 p=0.011), protein ($\geq$1 v. <1, HR=3.24, p=0.009), T stage (T4 v. TI-III, HR=2.99, p<0.049), race (Black v. White, HR=5.43, p<0.0001) and ethnicity (non-Hispanic vs. Hispanics, HR=3.00, p<0.014). Gender almost reached significance (female v. male, HR=2.39, p<0.072). Similarly significant predictors of overall survival were CD44$\geq$10 (HR=4.60, p=0.005), Protein$\geq$1 (HR=3.38, p=0.17), T4 stage (HR=2.97, p=0.035), Black race (HR=6.53, p<0.001) and Non-Hispanic ethnicity (HR=4.01, p=0.008). The following variables showed no significance as a predictor of progression-free survival and of overall survival: p16 status, CD44 staining pattern, EGFR staining pattern, keratinization, smoking history, alcohol history, site (oral cavity vs. oropharynx), node status, and age. Furthermore, CD44 and protein retained magnitude of effect and significance in bivariate analysis including disease stage.

In this group of HNSCC, only 5 subjects were never smokers; of these, 4 were HPV+. Of the HPV+ never smokers all were alive and 1 recurred. Thus the lack of association between p16 status and prognosis may be due to the few never smokers in the study as several studies show that HPV+ nonsmokers have a markedly better prognosis compared to HPV+ smokers.

To further investigate the significant associations between p16, CD44, and EGFR localization, immunofluorescence staining was performed. FIG. 6 shows typical p16-IHC staining where staining is cytoplasmic and diffuse. In this case, CD44 stains in the membrane and universally throughout the tumor. CD44 and EGFR colocalize on the cell membrane and there is some cytoplasmic staining of EGFR as well.

However, when tumors are p16+, as shown in FIG. 7, the nuclei stain strongly for p16 and there is some cytoplasmic staining as well. However, CD44 membrane staining is lost, only the invading lymphocytes retain CD44 expression. EGFR expression is not seen at all.

The methods of the appended claims are not limited in scope by the specific methods described herein, which are intended as illustrations of a few aspects of the claims and any methods that are functionally equivalent are within the scope of this disclosure. Various modifications of the methods in addition to those shown and described herein are intended to fall within the scope of the appended claims. Further, while only certain representative methods and aspects of these methods are specifically described, other methods and combinations of various features of the methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of characterizing a subject as being in need of treatment for head and neck squamous cell cancer (HNSCC), comprising:
   a) obtaining an oral rinse sample from the subject and separating the sample to a supernatant fraction and a pellet fraction;
   b) measuring with an immunoassay the level of solCD44 from the supernatant fraction;
   c) measuring with a protein assay the level of total protein from the supernatant fraction;
   d) lysing the pellet fraction and measuring the level of p16$^{INK4a}$ with an immunoassay; and
   e) characterizing whether the subject is in need of treatment for HNSCC based on results obtained in steps b) through d).

2. The method of claim 1, wherein the subject is characterized as being in need of treatment for HNSCC when the level of p16$^{INK4a}$ is higher than 15 U/mL, the level of solCD44 is higher than 2.7 ng/mL, and the level of total protein is higher than 1.0mg/mL.

3. A method of characterizing an oral rinse sample as being indicative of head and neck squamous cell cancer (HNSCC), comprising:
   a) obtaining an oral rinse sample from a subject and separating the sample to a supernatant fraction and a pellet fraction;
   b) measuring with an immunoassay the level of solCD44 from the supernatant fraction;
   c) measuring with a protein assay the level of total protein from the supernatant fraction;
   d) lysing the pellet fraction and measuring the level of p16$^{INK4a}$ with an immunoassay; and
   e) characterizing the oral rinse sample as being indicative of HNSCC based on results of step b) through d).

4. The method of claim 1, wherein the immunoassay used to measure the level of solCD44 is an Enzyme Linked Immunosorbent Assay.

5. The method of claim 1, wherein the immunoassay used to measure the level of solCD44 is a Lateral Flow Assay.

6. The method of claim 1, further comprising measuring the level of at least one of: hyaluronic acid (HA) and hyaluronidase (HAase) in the sample.

7. The method of claim 3, wherein the immunoassay used to measure the level of solCD44 is an Enzyme Linked Immunosorbent Assay.

8. The method of claim 3, wherein the immunoassay used to measure the level of solCD44 is a Lateral Flow Assay.

9. The method of claim 3, further comprising measuring the level of at least one of: hyaluronic acid (HA) and hyaluronidase (HAase) in the sample.

10. The method of claim 1, wherein a subject that has been characterized as being in need of treatment is given a single modality treatment.

11. The method of claim 10, wherein said single modality treatment comprises surgery, radiation, or chemotherapy.

12. The method of claim 3, wherein a subject that has been characterized as being in need of treatment is given a single modality treatment.

13. The method of claim 12, wherein said single modality treatment comprises surgery, radiation, or chemotherapy.

14. The method of claim 1, wherein a subject that has been characterized as being in need of treatment is given combined therapy.

15. The method of claim 14, wherein said combined treatment comprises at least two treatments comprising surgery, radiation, or chemotherapy treatment.

16. The method of claim 3, wherein a subject that has been characterized as being in need of treatment is given combined therapy.

17. The method of claim 16, wherein said combined treatment comprises at least two treatments comprising surgery, radiation, or chemotherapy treatment.

* * * * *